(12) United States Patent
Hazama

(10) Patent No.: US 11,179,162 B2
(45) Date of Patent: Nov. 23, 2021

(54) HEMOSTATIC DEVICE

(71) Applicant: TERUMO KABUSHIKI KAISHA, Tokyo (JP)

(72) Inventor: Kenichi Hazama, Bear, DE (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 40 days.

(21) Appl. No.: 16/238,966

(22) Filed: Jan. 3, 2019

(65) Prior Publication Data

US 2019/0133607 A1     May 9, 2019

Related U.S. Application Data

(63) Continuation of application No. PCT/JP2017/024383, filed on Jul. 3, 2017.

(30) Foreign Application Priority Data

Jul. 6, 2016  (JP) .............................. JP2016-134609

(51) Int. Cl.
| | | |
|---|---|---|
| *A61B 17/135* | (2006.01) | |
| *A61B 17/00* | (2006.01) | |
| *A61B 17/12* | (2006.01) | |

(52) U.S. Cl.
CPC .. *A61B 17/135* (2013.01); *A61B 2017/00862* (2013.01); *A61B 2017/12004* (2013.01)

(58) Field of Classification Search
CPC ........ A61F 5/012; A61F 5/05816; A61F 5/34; A61B 17/135; A61B 17/1325;

(Continued)

(56) References Cited

U.S. PATENT DOCUMENTS

| | | |
|---|---|---|
| 5,486,194 A | 1/1996 | Kawasaki et al. |
| 2004/0098035 A1 | 5/2004 | Wada et al. |

(Continued)

FOREIGN PATENT DOCUMENTS

| | | |
|---|---|---|
| CN | 105361920 A | 3/2016 |
| EP | 2685913 | 1/2014 |

(Continued)

OTHER PUBLICATIONS

Examination Report No. 1 dated Mar. 6, 2019 in corresponding Australian Patent Application No. 2017293690.

(Continued)

*Primary Examiner* — Katherine M Shi
(74) *Attorney, Agent, or Firm* — Buchanan Ingersoll & Rooney PC

(57) ABSTRACT

A hemostatic device is disclosed, which capable of favorably keeping strength of an inflatable portion and easily adjusting a discharge speed of gas. The hemostatic device includes a band for wrapping around a wrist, a fastener or means for securing that secures the band to the wrist in a wrapped state, an inflatable portion connected to the band and inflated by being injected with gas, and a filter member that controls discharge of gas injected into the inflatable portion, in which the band has one or more hole portions penetrating between an inner surface and an outer surface of the band, the inflatable portion is disposed to cover the hole portions on the inner surface of the band, and the filter member is disposed on the band to block the hole portions and controls discharge of gas from the hole portions.

20 Claims, 13 Drawing Sheets

(58) Field of Classification Search
CPC .... A61B 2017/12004; A61B 17/12009; A61B 17/12; A61B 17/132; A61B 17/1322; A61B 17/1355; A61B 2017/00557; A61L 2400/04

See application file for complete search history.

(56) References Cited

U.S. PATENT DOCUMENTS

| | | | |
|---|---|---|---|
| 2011/0077564 A1 | 3/2011 | Ganapathy et al. | |
| 2011/0190644 A1 | 8/2011 | Kohyama | |
| 2013/0085428 A1* | 4/2013 | Deshpande | A61H 9/0092 601/148 |
| 2014/0277102 A1* | 9/2014 | Mansur, Jr. | A61B 17/135 606/202 |
| 2015/0119773 A1 | 4/2015 | Flannery et al. | |

FOREIGN PATENT DOCUMENTS

| | | |
|---|---|---|
| JP | 747072 A | 2/1995 |
| JP | 2004201829 A | 7/2004 |
| JP | 2007021112 A | 2/2007 |
| JP | 2010088504 A | 4/2010 |
| WO | 2012/129146 A2 | 9/2012 |
| WO | 2015060967 A1 | 4/2015 |

OTHER PUBLICATIONS

The extended European Search Report dated Oct. 25, 2019, by the European Patent Office in corresponding European Patent Application No. 17824205.3-1122. (8 pages).

International Search Report (PCT/ISA/210) dated Oct. 31, 2017, by the Japanese Patent Office as the International Searching Authority for International Application No. PCT/JP2017/024383.

An English Translation of the International Search Report (Form PCT/ISA/210) and the Written Opinion of the International Searching Authority (Form PCT/ISA/237) dated Oct. 31, 2017, by the Japanese Patent Office in corresponding International Application No. PCT/JP2017/024383. (6 pages).

Office Action (Notification of the First Office Action) dated Dec. 1, 2020, by National Intellectual Property Administration, PRC in corresponding Chinese Patent Application No. 201780041789.7 and an English Translation of the Office Action. (13 pages).

* cited by examiner

HEMOSTATIC DEVICE

CROSS-REFERENCES TO RELATED APPLICATIONS

This application is a continuation of International Application No. PCT/JP2017/024383 filed on Jul. 3, 2017, which claims priority to Japanese Application No. 2016-134609 filed on Jul. 6, 2016, the entire contents of both of which is incorporated herein by reference.

FIELD OF THE INVENTION

The present disclosure generally relates to a hemostatic device for performing hemostasis by pressing a punctured site.

BACKGROUND DISCUSSION

Recently, percutaneous treatment/examination has been performed by puncturing a blood vessel of an arm or a leg, introducing an introducer sheath to a puncture site, and delivering a medical instrument such as a catheter to a lesion through a lumen of the introducer sheath. When such treatment/examination is performed, an operator needs to perform hemostasis in the puncture site after withdrawing the introducer sheath. To perform hemostasis, known hemostatic devices include a band for wrapping around a limb such as an arm or a leg, means for securing that secures the band in a state of being wrapping around the limb, and an inflatable portion connected to the band to press the puncture site by inflating in response to injection of a fluid into the inflatable portion.

In such a hemostatic device, when the inflating inflatable portion continues to strongly press the puncture site and a surrounding blood vessel or nerve for a relatively long time, there is a possibility of causing numbness, pain and/or occluding the blood vessel. In general, to prevent vascular occlusion, after inflating the inflatable portion, a doctor or a nurse regularly connects a dedicated instrument such as a syringe to the hemostatic device, discharges a fluid in the inflatable portion, and performs a depressurizing operation of depressurizing an internal pressure of the inflatable portion, which reduces a pressing force acting on the puncture site over time.

In a hemostatic device according to JP-A-2004-201829, an inflatable portion is made of a material that elongates over time. For this reason, after injecting a fluid into the inflatable portion, the inflatable portion is gradually inflated and transformed due to pressure from the fluid in the inflatable portion. Since the volume of an internal space of the inflatable portion gradually increases while the amount of the fluid in the inflatable portion does not greatly decrease, the internal pressure of the inflatable portion can be reduced over time. In this way, it is possible to reduce the pressing force acting on the puncture site over time.

According to the hemostatic device according to JP-A-2004-201829, it is possible to save labor of performing the depressurizing operation by the doctor or the nurse. However, when the inflatable portion is made of the material that elongates (i.e., stretches) over time, the inflatable portion is inflated and transformed over time, and thus a thickness of the inflatable portion decreases accordingly. From a viewpoint of favorably maintaining the strength of the inflatable portion, it is considered preferable that the thickness of the inflatable portion be maintained to some extent.

As a method to replace a decompression method utilizing a property of the material of the inflatable portion, for example, a method of forming a hole communicating with the internal space (inflatable space) of the inflatable portion in the band and discharging gas through the hole has been considered. However, in a case in which gas is discharged from the hole formed in the band, a discharge speed (i.e., discharge amount) of gas depends on the structure of the hole such as an internal diameter of the hole or the number of holes.

Since depressurization of the inflatable portion proceeds over time to such an extent that vascular occlusion can be prevented while a pressing force is applied to a puncture site P, it may be desirable that the discharge speed of gas is precisely controlled. As described above, in the case in which the hemostatic device is configured such that gas is discharged from the hole formed in the band, the discharge speed of gas needs to be controlled only by the structure of the hole, and thus it can be difficult to precisely control the discharge speed of gas. As a result, it is difficult for the hemostatic device to realize a desired depressurization protocol.

SUMMARY

A hemostatic device is disclosed, which is capable of favorably maintaining the strength of an inflatable portion and rather easily and precisely adjusting a discharge speed of gas from the hemostatic device.

A hemostatic device is disclosed, the hemostatic device including a band for wrapping around a site where bleeding is to be stopped of a limb, means for securing that secures the band to the limb in a wrapped state, an inflatable portion connected to the band and inflated by being injected with gas, and a filter member that controls discharge of gas injected into the inflatable portion, in which the band has one or more hole portions penetrating between an inner surface and an outer surface of the band, the inflatable portion is disposed to cover the hole portions on the inner surface of the band, and the filter member is disposed on the band to block the hole portions and controls discharge of gas from the hole portions.

As described above, the hole portions are provided in a region in which the inflatable portion of the band is disposed, and the filter member blocks the hole portions to control a discharge amount of gas injected into the inflatable portion. For this reason, it is unnecessary to make the thickness of the inflatable portion relatively thin to increase the gas permeation amount, and the strength of the inflatable portion can be favorably kept. In addition, since the discharge speed of gas injected into the inflatable portion is controlled by the filter member, the discharge speed of gas can be rather easily and precisely adjusted when compared to a case in which the discharge speed of gas is controlled only by a structure of the hole provided in the band. Further, since the filter member is disposed on the band to block the hole portion, the filter member is supported by the band, and transformation of the filter member can be suppressed. In this way, the discharge speed of gas is less likely to receive an influence of transformation of the filter member to change, and thus the hemostatic device may realize a desired depressurization protocol.

A hemostatic device is disclosed comprising: a band configured to be wrapped around a puncture site where bleeding is to be stopped, the band having one or more hole portions penetrating between an inner surface and an outer surface of the band; a fastener configured to securing the band to a limb in a wrapped state; an inflatable portion configured to be connected to the band and inflated with a gas, the inflatable portion being disposed to cover the one or more hole portions on the inner surface of the band; and a filter member disposed on the band to block the one or more hole portions and configured to control discharge of the gas from the inflatable portion through the one or more hole portions.

A hemostatic device is disclosed comprising: a band configured to be disposed on a puncture site of a limb where bleeding is to be stopped, the band including a support plate on which the inflatable portion is disposed and a holding portion that holds the support plate with respect to the limb, the support plate having a hole portion penetrating between an inner surface and an outer surface of the support plate; an inflatable portion configured to be connected to the band and inflated with a gas; and a filter member configured to control discharge of the gas injected into the inflatable portion, the filter member being disposed between the inflatable portion and the support plate.

A method is disclosed for performing hemostasis on a puncture site of a blood vessel of a patient's limb, the method comprising: wrapping a band of a hemostatic device around the patient's limb having the puncture site, the band having one or more hole portions penetrating between an inner surface and an outer surface of the band, and the hemostatic device also having an inflatable portion configured to be connected to the band and inflated with a gas, the inflatable portion being disposed to cover the one or more hole portions on the inner surface of the band, and a filter member disposed on the band to block the one or more hole portions and configured to control discharge of the gas from the inflatable portion through the one or more hole portions; and securing the band to the patient's limb in a wrapped state.

BRIEF DESCRIPTION OF THE DRAWINGS

FIGS. 14A and 14 are an enlarged cross-sectional view illustrating the backflow check structure of the hemostatic device according to Modification 4, wherein FIG. 14A is a diagram illustrating a state in which air is injected into an inflatable portion.

DETAILED DESCRIPTION

Figure 1:
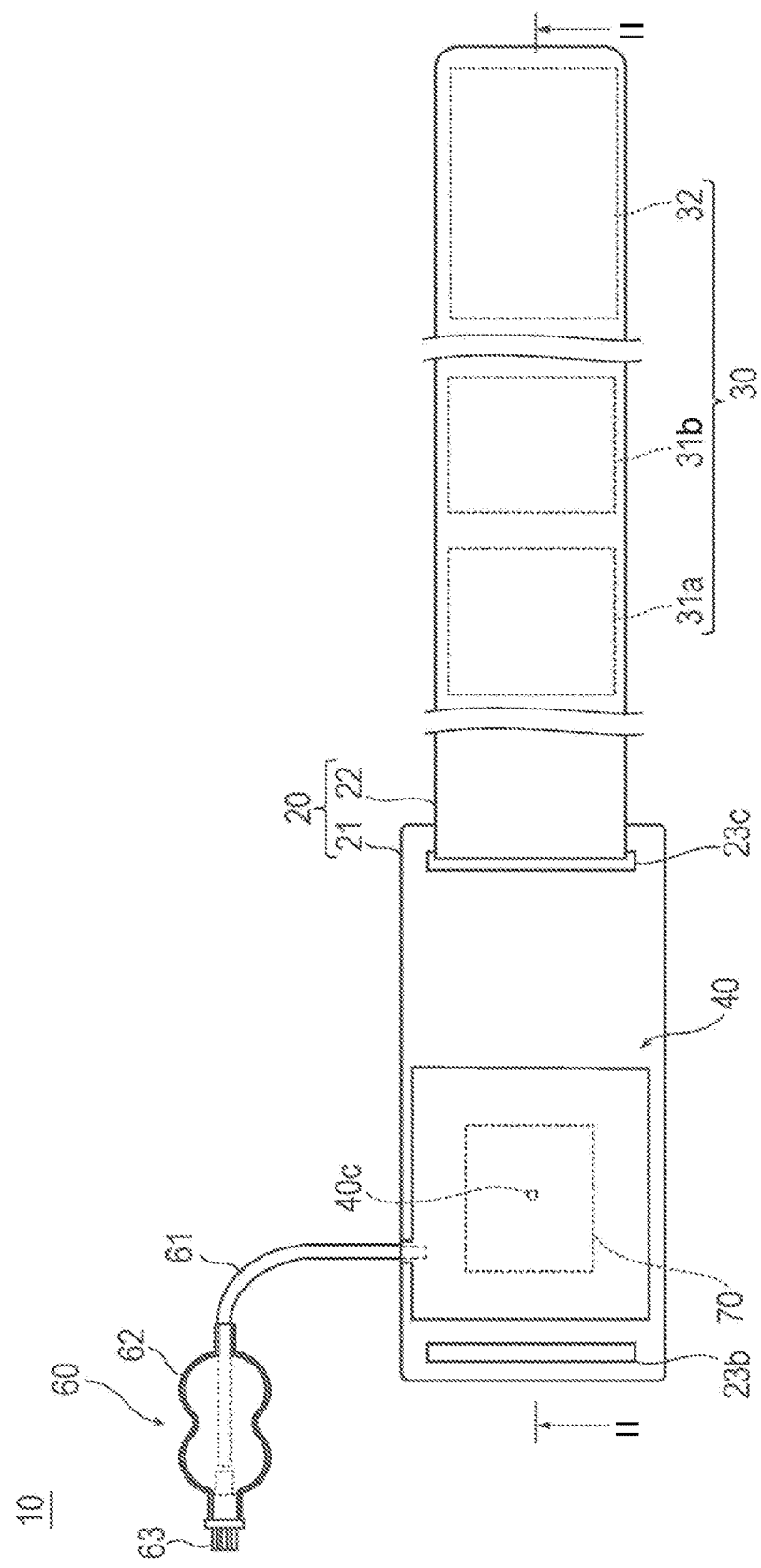
FIG. 1 is a plan view of a hemostatic device according to an embodiment viewed from an inner surface side.

Hereinafter, an embodiment and modifications of the embodiments of the disclosure will be described with reference to accompanying drawings. Note that a description below does not restrict a technical scope or a meaning of a term described in claims. In addition, a ratio of dimensions in the drawings is exaggerated for convenience of description and may be different from an actual ratio.

Figure 2:
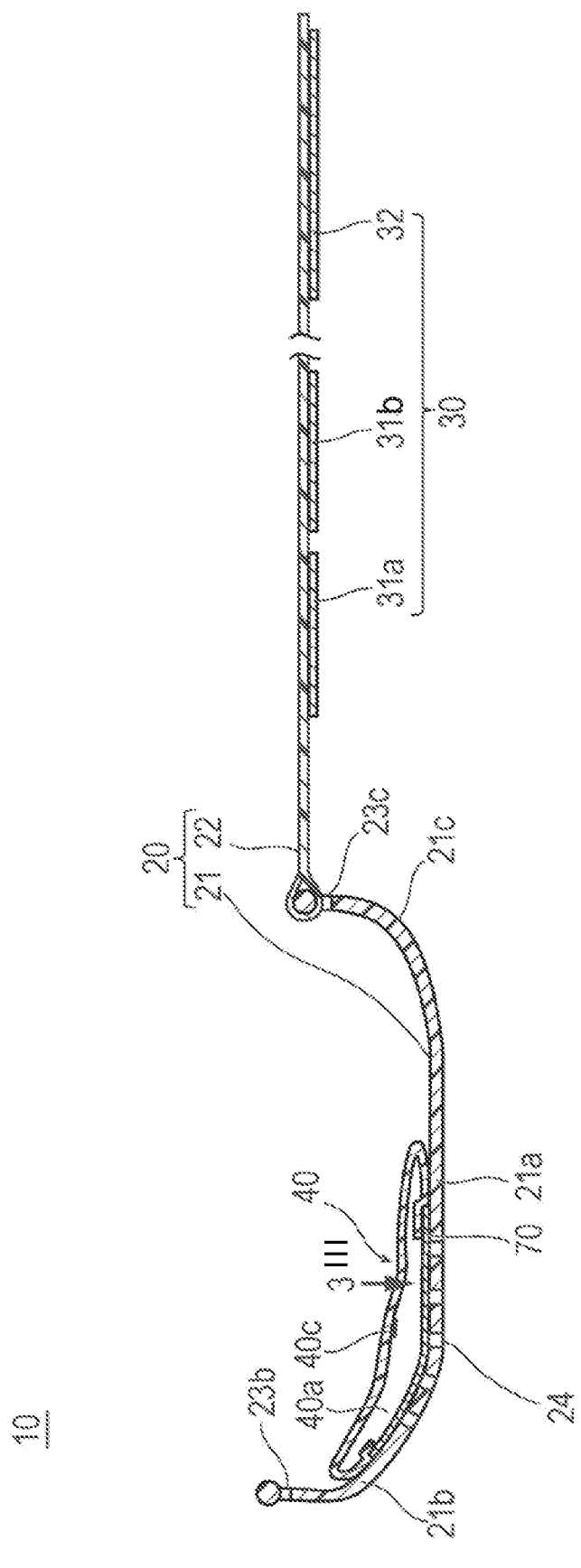
FIG. 2 is a cross-sectional view taken along line II-II of FIG. 1.
Figure 3:
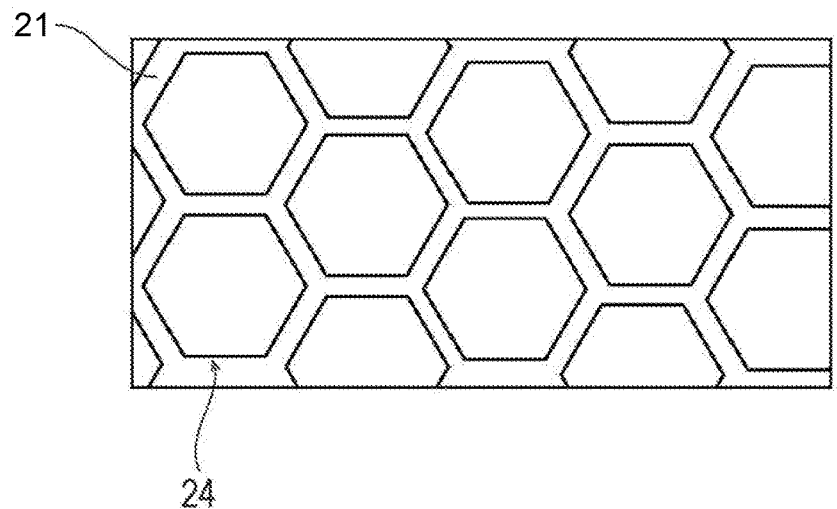
FIG. 3 is an enlarged plan view of a hole portion viewed in a direction of an arrow III of FIG. 2.
Figure 4:
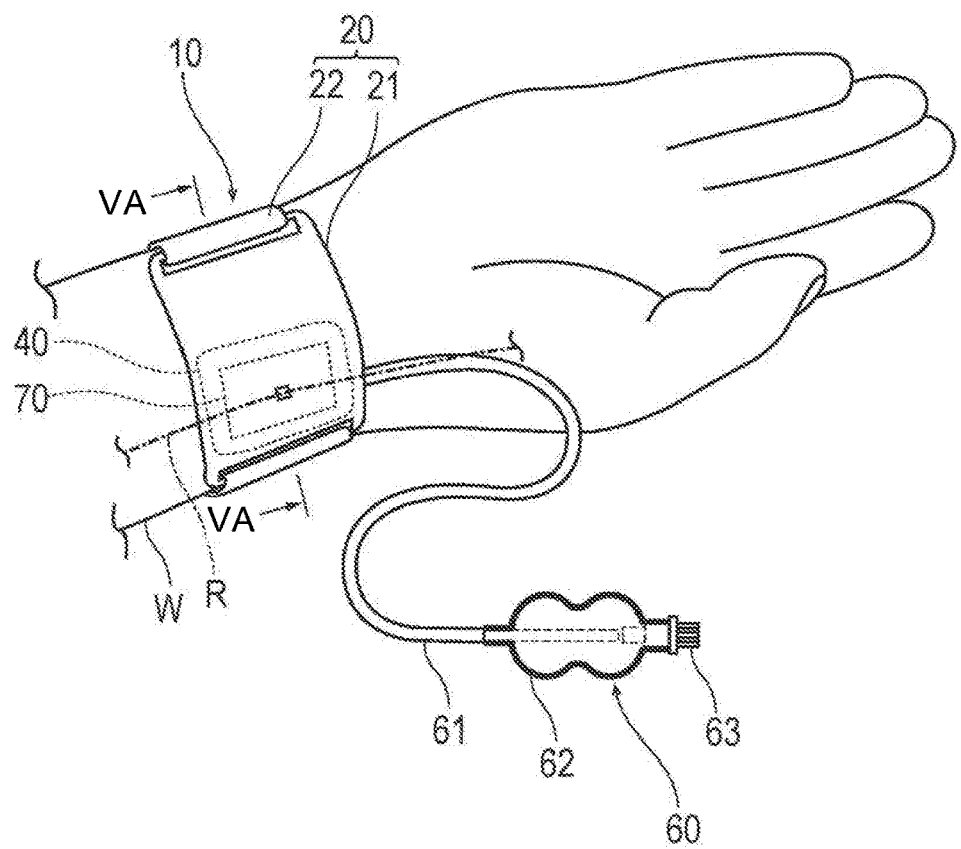
FIG. 4 is a perspective view illustrating a state in which the hemostatic device according to the embodiment is mounted on a wrist.
Figure 5A:
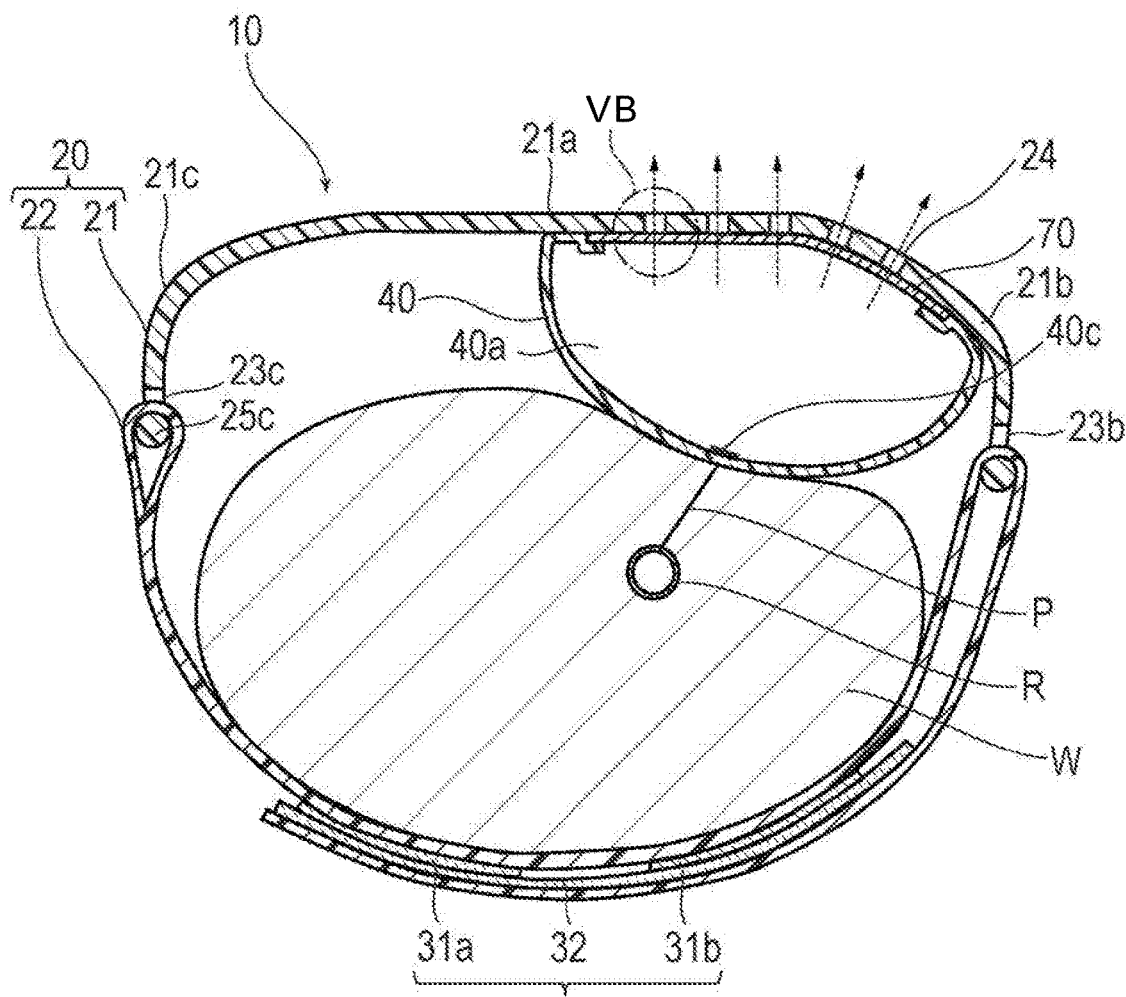
FIG. 5A is a cross-sectional view taken along line VA-VA of FIG. 4.
Figure 5B:
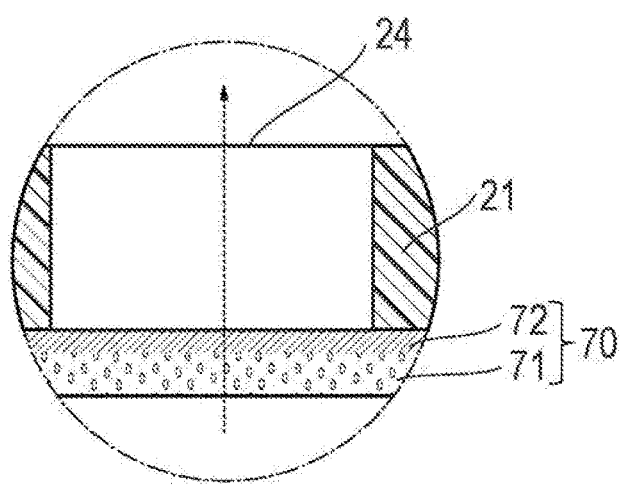
FIG. 5B is an enlarged view of part VB of FIG. 5A.

A hemostatic device 10 according to the present exemplary embodiment will be described with reference to FIGS. 1-5B. FIGS. 1-3 are diagrams for description of each portion of the hemostatic device 10. FIGS. 4, 5A, and 5B are diagrams for description of a use example of the hemostatic device 10.

As illustrated in FIGS. 4 and 5A, to insert a catheter, for example, for performing treatment/examination, into a blood vessel, after withdrawing an introducer sheath indwelled in a puncture site P (corresponding to a "site where bleeding is to be stopped") formed in a radial artery R of a wrist W (corresponding to a "limb"), the hemostatic device 10 according to the embodiment is used to stop bleeding in the puncture site P.

As illustrated in FIGS. 1 and 2, the hemostatic device 10 can include a band 20 for wrapping around the wrist W, a surface fastener 30 (corresponding to "means for securing" (securing member)) that secures the band 20 in a state of being wrapped around the wrist W, an inflatable portion 40 that inflates by being injected with a gas and presses the puncture site P, a marker 40c for positioning the inflatable portion 40 in the puncture site P, an injection part 60 capable of injecting gas into the inflatable portion 40, and a filter member 70 that controls discharge of gas injected into the inflatable portion 40.

In the present disclosure, when the band 20 is wrapped around the wrist W, a surface (mounting surface) of the band 20 facing a body surface of the wrist W is referred to as an "inner surface", and a surface on an opposite side is referred to as an "outer surface".

The band 20 can include a support plate 21 (corresponding to a "support body portion") on which the inflatable portion 40 is disposed, and a belt 22 (corresponding to a "holding portion"), which is connected to the support plate 21 and on which the means for securing (i.e., fastener) 30 is disposed to hold the support plate 21 with respect to the wrist W.

The support plate 21 is disposed along a circumferential direction of the wrist W. As illustrated in FIG. 2, a central portion 21a in a longitudinal direction of the support plate 21 has a flat plate shape with little curvature. A first curved portion 21b (left side of FIG. 2) and a second curved portion 21c (right side of FIG. 2) curved toward the inner surface side and along the longitudinal direction of the support plate 21 (circumferential direction of the wrist W) are formed on both sides of the central portion 21a, respectively. In accordance with an exemplary embodiment, the support plate 21 is made of a material more rigid than that of the belt 22 and is designed to maintain a substantially constant shape.

A through-hole 23b penetrating the support plate 21 in a thickness direction is provided at an end portion of the support plate 21 on a side where the first curved portion 21b is provided. A through-hole 23c penetrating the support plate 21 in the thickness direction is provided at an end portion of the support plate 21 on a side where the second curved portion 21c is provided. As illustrated in FIG. 1, each of the through-holes 23b and 23c extends along a width direction of the support plate 21 (a direction intersecting the longitudinal direction of the support plate 21). The belt 22 is connected to the end portion of the support plate 21 in a state of being inserted into the through-hole 23c on the second curved portion 21c side. When the hemostatic device 10 is mounted on the wrist W, as illustrated in FIG. 5A, the belt 22 is inserted into the through-hole 23b on the first curved portion 21b side. The belt 22 inserted into the through-hole 23b on the first curved portion 21b side is folded back and wrapped around a part of an outer periphery of the wrist W.

As illustrated in FIGS. 3 and 5A, a plurality of hole portions 24 penetrating between the inner surface and the outer surface of the support plate 21 (that is, penetrating the support plate 21 in the thickness direction) is provided in a region in which the inflatable portion 40 of the support plate 21 is disposed. Note that even though the number of hole portions 24 is omitted in the illustrations (FIGS.), a large number of hole portions 24 can be formed in the support plate 21 as illustrated in FIG. 3.

For example, shapes, sizes, and the number of the hole portions 24 may be set in consideration of the strength of the support plate 21, a permeation amount of gas, and risk of damage to the filter member 70 coming into contact with the support plate 21. In accordance with an exemplary embodiment, to keep the strength of the support plate 21 relatively high, it may be preferable that the number of hole portions 24 is relatively small, and the sizes of hole portions 24 are relatively small in plan view from the inner surface side of the support plate 21 (that is, a contact area between the hole portions 24 and the filter member 70 is relatively small) as illustrated in FIG. 3. On the other hand, to keep the permeation amount of gas high, it can be preferable that the number of hole portions 24 is relatively large, and the sizes of hole portions 24 are relatively large in plan view from the inner surface side of the support plate 21 (that is, the contact area between the hole portions 24 and the filter member 70 is large). In addition, to prevent the filter member 70 from being damaged, it can be preferable that each of the hole portions 24 has a shape close to a round shape in plan view from the inner surface side of the support plate 21. For example, when the hole portion 24 is formed in a rectangular shape, stress is liable to be locally applied to a part of the filter member 70 in a part in which a corner portion (edge) of a circumference of the hole portion 24 comes into contact with the filter member 70, and thus there is a possibility that the filter member 70 may be damaged.

In consideration of the above, in the present embodiment, as illustrated in FIG. 3, the hole portion 24 is formed to have a shape of a regular hexagon in plan view from the inner surface side of the support plate 21. When the hole portion 24 is formed to have the shape of the regular hexagon in plan view, the hole portions 24 may be densely arranged without forming a large gap between adjacent hole portions 24. In addition, since the shape in plan view is a shape close to a round shape having no corner portion, damage to the filter member 70 due to a corner portion can be prevented.

Since the hole portions 24 penetrate the support plate 21 in the thickness direction, a honeycomb structure including the plurality of hole portions 24, each of the plurality of hole portions 24 being formed to have a shape of a regular hexagon, is formed in the region in which the inflatable portion 40 of the support plate 21 is disposed. The honeycomb structure formed by the plurality of hole portions 24 keeps the strength of the support plate 21 relatively high when compared to a case in which a plurality of holes having, for example, simple circular shapes, is formed. In addition, when the honeycomb structure is adopted, the respective hole portions 24 are arranged without gaps, and thus the permeation amount of gas may be suitably maintained.

Note that the shape of the hole portion 24 in plan view is not limited only to the regular hexagon, and may correspond to, for example, a shape of a polygon other than the regular hexagon, a circular shape, or an elliptical shape. In addition, a cross section of the hole portion 24 along the thickness direction of the support plate 21 is not illustrated. However, in the present embodiment, a cross-sectional shape is formed to be a constant shape without changing along the thickness direction.

The support plate 21 material is a material having a higher elastic modulus than that of the belt 22 and the inflatable portion 40. Examples of the material of the support plate 21 can include acrylic resins, polyvinyl chloride (particularly rigid polyvinyl chloride), polyolefins such as polyethylene, polypropylene and polybutadiene, polystyrene, poly(4-methyl pentene-1), polycarbonates, ABS resins, polymethyl methacrylate (PMMA), polyacetals, polyacrylates, polyacrylonitriles, polyvinylidene fluorides, ionomers, acrylonitrile-butadiene-styrene copolymers, polyesters such as polyethylene terephthalate (PET) and polybutylene terephthalate (PBT), butadiene-styrene copolymers, aromatic or aliphatic polyamides, and fluorocarbon resins such as polytetrafluoroethylene.

It is preferable that a part of the support plate 21 overlapping the inflatable portion 40 is substantially transparent. However, the part of the support plate 21 may not be transparent, and may be translucent or colored transparent. In this way, the puncture site P may be reliably visually recognized from the outer surface side, and the marker 40c described below may be easily positioned in the puncture site P. Note that the support plate 21 may not have a flat plate-shaped portion as the central portion 21a, and may be curved over an entire length of the support plate 21.

Female sides 31a and 31b of the surface fastener 30 are disposed on a side of the belt 22 connected to the support plate 21 (left side of FIG. 1 and FIG. 2). A male side 32 of the surface fastener 30 is disposed on a side of the belt 22 not connected to the support plate 21 (right side of FIG. 1 and FIG. 2). For example, the surface fastener 30 is a hook and loop fastener known as a general product such as VELCRO® or Magic Tape®.

When the hemostatic device 10 is mounted on the wrist W, as illustrated in FIG. 5A, the belt 22 is mounted along a part of the outer periphery of the wrist W while being folded back at the through-hole 23b of the support plate 21. In this way, the male side 32 may be disposed to face each of the female sides 31a and 31b. In this instance, when a length in which the band 20 is folded back is adjusted according to a length (thickness) of the outer periphery of the wrist W of the wearer, the hemostatic device 10 may be appropriately mounted regardless of the length of the outer periphery of the wrist W of the wearer. The hemostatic device 10 is mounted on the wrist W by joining each of the female sides 31a and 31b and the male side 32 together. In accordance with an exemplary embodiment, the female sides 31a and 31b are more flexible than the male side 32, and thus discomfort given to the wearer can be relatively suppressed or reduced by disposing the female sides 31a and 31b at positions close to the outer surface of the wrist W.

Note that, for example, the surface fastener 30 may include one female side and one male side, and a position of the female side and a position of the male side may be exchanged. In addition, means for securing the band 20 to the wrist W in a wrapped state is not limited to the surface fastener 30. For example, it is possible to use a securing member such as a snap, a button, or a clip.

The belt 22 material is not particularly limited as long as the material of the belt 22 has flexibility. Examples of the material of the belt 22 can include polyvinyl chloride, polyolefins such as polyethylene, polypropylene, polybutadiene and ethylene-vinyl acetate copolymers (EVA), polyesters such as polyethylene terephthalate (PET) and polybutylene terephthalate (PBT), polyvinylidene chloride, silicone, polyurethane, various thermoplastic elastomers such as polyamide elastomers, polyurethane elastomers and polyester elastomers, and an arbitrary combination of the above (blend resin, polymer alloy, laminate, etc.).

The inflatable portion 40 inflates by being injected with gas, and has a function of applying a pressing force to the puncture site P. Note that the gas injected into the inflatable portion 40 is not particularly limited as long as the inflatable portion 40 can be inflated. For example, air can be used to inflate the inflatable portion 40.

In accordance with an exemplary embodiment, the inflatable portion 40 is formed of a substantially rectangular sheet. As illustrated in FIG. 3, the inflatable portion 40 is disposed to cover a region in which the hole portion 24 is provided on the inner surface side of the support plate 21. An outer peripheral edge portion of the inflatable portion 40 is joined to the support plate 21 and an outer peripheral edge portion of the filter member 70 disposed to block the hole portion 24 provided in the support plate 21 as described below in a state of being tucked in to the support plate 21 side. For this reason, an outer peripheral edge of the filter member 70 may be pressed by the inflatable portion 40, and the filter member 70 is less likely to peel off from the support plate 21. Note that, for example, joining may be performed by a method such as welding or adhesion using an adhesive. In addition, an external shape of the inflatable portion 40 is not limited to a rectangular shape, and may correspond to a round shape or a polygonal shape.

An inflatable space 40a into which gas is injected is formed between the inflatable portion 40 and the filter member 70.

As illustrated in FIGS. 5A and 5B, the inflatable portion 40 is disposed on the inner surface side of the band 20. For this reason, when the inflatable portion 40 is inflated, a pressing force of the inflatable portion 40 is concentrated on the wrist W side, and it is possible to suitably apply the pressing force to the puncture site P. In addition, since the inflatable portion 40 is pressed against the wrist W by the band 20 to increase an internal pressure, it is possible to suitably discharge gas in the inflatable portion 40 to the outside through the hole portions 24 of the support plate 21 and the filter member 70 as described below.

The inflatable portion 40 material is not particularly limited as long as the material has a lower elastic modulus than that of the support plate 21 and is relatively flexible. For example, the material of the inflatable portion 40 can be the same material as the material of the belt 22.

It is preferable that the inflatable portion 40 is substantially transparent. However, the inflatable portion 40 may not be transparent, and may be translucent or colored transparent. In this way, the puncture site P may be visually recognized from the outer surface side, and the marker 40c described below may be relatively easily positioned in the puncture site P.

As illustrated in FIG. 2, the marker 40c can be provided substantially at a center of a surface of the inflatable portion 40 facing the support plate 21. For this reason, the inflatable portion 40 may be rather easily positioned with respect to the puncture site P, and position shift of the inflatable portion 40 can be suppressed or reduced. In addition, the marker 40c may be prevented from directly coming into contact with the puncture site P. Note that a position at which the marker 40c is provided is not particularly limited as long as the inflatable portion 40 may be positioned in the puncture site P. For example, the marker 40c may be provided on the filter member 70 or the support plate 21 as long as discharge of gas by the hole portions 24 is not hindered.

A shape of the marker 40c is not particularly limited, and examples of the shape of the marker 40c can include, for example, a circle, a triangle, or a quadrangle. In present embodiment, the shape corresponds to the quadrangle.

A size of the marker 40c is not particularly limited. For example, when the shape of the marker 40c corresponds to the quadrangle, it is preferable that a length of one side of the marker 40c is in a range of 1 mm to 4 mm. When the length of the one side of the marker 40c is 5 mm or more, the size of the marker 40c increases with respect to a size of the puncture site P, and thus it can be difficult to position a central portion of the inflatable portion 40 in the puncture site P.

The marker 40c material is not particularly limited. Examples of the marker 40c material can include, for example, an oily coloring agent such as ink or a resin kneaded with a pigment.

The marker 40c color is not particularly limited when the color allows the inflatable portion 40 to be positioned in the puncture site P. However, a green-based color is preferable. When the green-based color is adopted, it can be relatively easy to visually recognize the marker 40c on blood or skin, and thus the inflatable portion 40 can be rather easily positioned in the puncture site P.

In addition, the marker 40c is preferably translucent or colored transparent. In this way, the puncture site P may be visually recognized from the outer surface side of the band 20.

A scheme of providing the marker 40c on the inflatable portion 40 is not particularly limited. Examples of the marker 40c scheme can include printing the marker 40c on the inflatable portion 40, and applying an adhesive to one surface of the marker 40c to paste the marker 40c to the inflatable portion 40.

The injection part 60 corresponds to a site for injecting gas into the inflatable portion 40, and is connected to the inflatable portion 40 as illustrated in FIG. 1.

A proximal portion of the injection part 60 is disposed between the inflatable portion 40 and the filter member 70, and a lumen of the injection part 60 includes a tube 61 having flexibility communicating with the inflatable space 40a of the inflatable portion 40, a bag body 62 disposed at a distal portion of the tube 61 to communicate with a lumen of the tube 61, and a tube-shaped connector 63 incorporating a check valve (not illustrated) connected to the bag body 62.

At the time of inflating (expanding) the inflatable portion 40, a tip of a syringe (not illustrated) is inserted into the connector 63 to open a check valve, and a plunger of this syringe is pushed to inject gas in the syringe into the inflatable portion 40 through the injection part 60. When the inflatable portion 40 inflates, the bag body 62 communicating with the inflatable portion 40 through the tube 61 also inflates, and it is possible to visually confirm that the inflatable portion 40 can be pressed without leakage of gas. When the tip of the syringe is withdrawn from the connector 63 after gas is injected into the inflatable portion 40, the check valve incorporated in the connector 63 is closed to prevent leakage of gas.

The filter member 70 has a function of controlling a discharge speed at which the gas injected into the inflatable portion 40 is discharged to the outside of the inflatable portion 40.

As illustrated in FIG. 1, the filter member 70 can include a substantially rectangular sheet. As illustrated in FIG. 2, the filter member 70 is joined to the inner surface of the support plate 21 to block the hole portions 24. Therefore, the filter member 70 is disposed between the support plate 21 and the inflatable portion 40. For this reason, it is possible to prevent the filter member 70 from being exposed to the outside and thus, prevent, for example, the wearer or a peripheral medical instrument from coming into contact with the filter member to damage the filter member 70. In addition, it is possible to help prevent the filter member 70 from coming into contact with the wearer or the peripheral medical instrument, which can hinder (i.e., prevent) a gas discharge function of the filter member 70. Note that an external shape of the filter member 70 is not particularly limited as long as the hole portions 24 can be blocked. For example, it is possible to adopt a round shape, or a polygonal shape other than the quadrangle.

In the present embodiment, as illustrated in FIG. 5B, the filter member 70 has an asymmetric membrane including a porous layer 71 and a skin layer 72 having a larger gas permeation amount per unit area than that of the porous layer 71.

In the present embodiment, the porous layer 71 has a relatively larger thickness than that of the skin layer 72. The porous layer 71 serves to favorably keep the strength of the entire filter member 70 by supporting the skin layer 72, which is a relatively thin layer. In addition, the porous layer 71 includes a large number of holes. In the present embodiment, the porous layer 71 includes a hole having a size of 1 nm or greater.

The number of holes per unit area of the skin layer 72 is smaller than that of the porous layer 71. In this way, the gas permeation amount per unit area of the skin layer 72 is smaller than that of the porous layer 71. Note that a magnitude relation of a gas permeation amount between the skin layer 72 and the porous layer 71 may be adjusted by the number of holes, a diameter of the hole, and/or a shape of the hole provided in both layers.

In the present embodiment, the skin layer 72 does not include a hole having a size of 1 nm or greater. For this reason, the gas injected into the inflatable portion 40 permeates the skin layer 72 due to a dissolution/diffusion phenomenon. In addition, in the present embodiment, the inflatable portion 40 and the filter member 70 are formed of the same material, and a thickness of the skin layer 72 is smaller than a thickness of the inflatable portion 40. Therefore, the gas injected into the inflatable portion 40 is mainly discharged to the outside through the filter member 70, and the discharge speed mainly depends on the gas permeation amount of the skin layer 72.

As described above, discharge of the gas injected into the inflatable portion 40 is mainly performed through the hole portions 24 provided in the band 20 and the filter member 70. For this reason, it is unnecessary to make the thickness of the inflatable portion 40 relatively thin to increase the gas permeation amount, such that the strength of the inflatable portion 40 can be favorably kept. In addition, to control discharge of the gas injected into the inflatable portion 40, the filter member 70 may suppress discharge of the gas when compared to a case in which the gas is discharged from the hole portions 24 provided in the band 20 (a case in which the hole portions 24 are not blocked by the filter member 70). That is, the discharge speed of the gas injected into the inflatable portion 40 may be relatively easily and precisely adjusted by the filter member 70.

Note that the filter member 70 includes the skin layer 72 which is a relatively thin layer and can be easily damaged, and has a smaller elastic modulus than that of the support plate 21 and the inflatable portion 40, and wherein the inflatable portion 40 has a relatively high flexibility. For this reason, the filter member 70 can be damaged relatively easily due to, for example, transformation or change of the inflatable portion 40. However, in the present embodiment, the filter member 70 is disposed on the support plate 21 having a relatively high elastic modulus and supported by the support plate 21, and thus, it is possible to help prevent the filter member 70 from damaging the skin layer 72 from transformation or changes to the inflatable portion.

In accordance with an exemplary embodiment, it can be preferable that a gas permeation speed of the filter member 70 as a whole is formed to realize a depressurization protocol satisfying the following Conditions 1 and 2.

Condition 1—When gas is discharged to the outside of the inflatable portion 40 through the filter member 70 and the hole portions 24 over four hours after inflation in a state in which the band 20 is wrapped around the wrist W, an internal pressure of the inflatable portion 40 at every lapse of one hour is 70% to 97% (preferably 75% to 94%) of an internal pressure of the inflatable portion 40 before one hour; and Condition 2—An internal pressure in the inflatable portion 40 after four hours elapse after inflation in the state in which the band 20 is wrapped around the wrist W is 30% to 80% (preferably 40% to 71%) of an initial internal pressure.

To satisfy the above conditions, it is necessary to set the thickness of the filter member 70 and the size of the hole portion 24 of the support plate 21 at a suitable time. However, when 18 ml of gas is injected into the inflatable portion 40 so that an internal pressure of the inflatable space 40a of the inflatable portion 40 becomes 40 kPa to 50 kPa (300 mmHg to 375 mmHg), it is preferable that the gas permeation amount per hour of the filter member 70 is 0.5 ml to 3.0 ml. In addition, a thickness of the porous layer 71 may be set to, for example, 10 μm to 1 mm, and a thickness of the skin layer 72 may be set to, for example, 100 nm to several μm.

Note that the filter member 70 may have a function of controlling the discharge speed at which the gas injected into the inflatable portion 40 is discharged to the outside of the inflatable portion 40. For this reason, the filter member 70 can be substituted, for example, by using a material having a larger gas permeation amount per unit area than that of the material of the inflatable portion 40.

Next, a description will be given of a method of using the hemostatic device 10 according to the present embodiment.

Before the hemostatic device 10 is mounted on the wrist W, as illustrated in FIG. 2, the inflatable portion 40 is in a state of not being inflated. As illustrated in FIGS. 4 and 5A, when the radial artery R of the right hand wrist W is punctured, the puncture site P is at a position biased to a thumb side. Normally, the introducer sheath is indwelled in the puncture site P. The band 20 is wrapped around the wrist W in which the introducer sheath is indwelled, the inflatable portion 40 and the band 20 are positioned such that the marker 40c provided on the inflatable portion 40 overlaps the puncture site P, and the female sides 31a and 31b and the male side 32 of the surface fastener 30 are brought into contact with each other and joined to each other, thereby mounting the band 20 on the wrist W.

In this instance, the hemostatic device 10 is mounted on the wrist W such that the injection part 60 faces a downstream side (palm side) of a blood flow of the radial artery R. In this way, the injection part 60 may be operated without interfering with manipulation on the upstream side of the wrist or a device (for example, a sphygmomanometer) located on the upstream side. In addition, when the hemostatic device 10 is mounted on the right hand wrist W such that the injection part 60 faces the downstream side, the inflatable portion 40 is located on the radial artery R biased to the thumb side of the wrist W. Note that in the case of the artery, the upstream side (proximal side) of the blood vessel refers to a direction of the blood vessel approaching a heart. In addition, the downstream side (distal side) of the blood vessel refers to a direction of the blood vessel away from the heart.

Note that the hemostatic device 10 may be used for puncturing the radial artery of the left hand wrist. In this case, the injection part 60 is mounted on the left hand wrist to face the upstream side of the blood flow of the radial artery.

After the hemostatic device 10 is mounted on the wrist W, the syringe (not illustrated) is connected to a connector 63 of the injection part 60, gas is injected into the inflatable portion 40 as described above, and the inflatable portion 40 is inflated.

A degree of inflation of the inflatable portion 40, that is, a pressing force acting on the puncture site P may be easily adjusted depending on the case according to an injection amount of gas at this time. For example, when gas is excessively injected into the inflatable portion 40, and thus the inflatable portion 40 is excessively inflated, excessively injected gas may be discharged from the inside of the inflatable portion 40 using the syringe. After the inflatable portion 40 is inflated, the syringe is detached from the connector 63. Then, the introducer sheath is withdrawn from the puncture site P.

After the inflatable portion 40 is inflated, while a pressing force is applied to the puncture site P mainly through the filter member 70 and the hole portions 24 of the support plate 21, gas in the inflatable portion 40 is discharged to the outside of the inflatable portion 40 over time as indicated by broken arrows of FIGS. 5A and 5B to such an extent that vascular occlusion can be prevented.

Note that when hemostasis is not sufficiently performed after inflation of the inflatable portion 40, gas may be injected into the inflatable portion 40 to raise the internal pressure of the inflatable portion 40. For example, when it is desirable to return the internal pressure of the inflatable portion 40 to the internal pressure at the time of injecting gas into the inflatable portion 40, gas discharged from the inflatable portion 40 may be injected.

When a predetermined time elapses, and hemostasis of the puncture site P is completed, the hemostatic device 10 is removed from the wrist W. The hemostatic device 10 is removed from the wrist W by peeling off the female sides 31a and 31b and the male side 32 of the surface fastener 30.

As described above, the hemostatic device 10 according to the present embodiment includes the band 20 for wrapping around the puncture site P, the means for securing 30 that secures the band 20 in the state of being wrapped around the wrist W, the inflatable portion 40 which is connected to the band 20 and inflates by being injected with gas, and the filter member 70 that controls discharge of gas injected into the inflatable portion 40. The band 20 has one or more hole portions 24 penetrating between the inner surface and the outer surface of the band 20. The inflatable portion 40 is disposed to cover the hole portion 24 on the inner surface of the band 20. The filter member 70 is disposed on the band 20 to block the hole portion 24 and controls discharge of gas from the hole portion 24.

As described above, the hole portion 24 is provided in the region in which the inflatable portion 40 of the band 20 is disposed, and the filter member 70 controls the discharge amount of gas injected into the inflatable portion 40 by blocking the hole portion 24. For this reason, it is unnecessary to make the thickness of the inflatable portion 40 relatively thin to increase the gas permeation amount, and the strength of the inflatable portion 40 can be favorably kept. In addition, since the discharge speed of gas injected into the inflatable portion 40 is controlled by the filter member 70, it is possible to easily and precisely adjust the discharge speed of gas when compared to a case in which the discharge speed of gas is controlled only by a structure of the hole provided in the band 20. Further, since the filter member 70 is disposed on the band 20 to block the hole portion 24, the filter member 70 is supported by the band 20, and transformation of the filter member 70 is suppressed. In this way, the discharge speed of gas is less likely to receive an influence of transformation of the filter member 70 to change, and thus the hemostatic device 10 may realize a desired depressurization protocol.

In addition, the band 20 includes the support plate 21 on which the inflatable portion 40 is disposed and the belt 22 on which the means for securing 30 is disposed, and the elastic modulus of the support plate 21 is relatively higher than that of the inflatable portion 40 and the belt 22. For this reason, it is possible to suitably prevent transformation of the filter member 70 disposed to block the hole portion 24 formed in the support plate 21 while suitably inflating and transforming the inflatable portion 40. That is, even when the inflatable portion 40 is inflated, a gas permeation function of the filter member 70 may be suitably maintained.

In addition, the filter member 70 is disposed between the inflatable portion 40 and the band 20. For this reason, the filter member 70 is prevented from coming into contact with the wearer and/or a peripheral medical instrument and being damaged. In addition, the filter member 70 is prevented from coming into contact with the wearer and/or the peripheral medical instrument and hindering the gas discharge function of the filter member 70.

In addition, the inflatable portion 40 is joined to the outer peripheral edge portion of the filter member 70. For this reason, it is possible to suitably prevent the filter member 70 from being inadvertently separated or dropped from the band 20.

In addition, the material of the filter member 70 has a larger gas permeation amount per unit area than that of the material of the inflatable portion 40. For this reason, the filter member 70 may control the discharge speed of gas injected into the inflatable portion 40 by the filter member 70.

In addition, the filter member 70 and the inflatable portion 40 are formed of the same material, and the filter member 70 includes the porous layer 71 and the skin layer 72 having a larger gas permeation amount per unit area than that of the porous layer 71. For this reason, the filter member 70 may control the discharge speed of gas injected into the inflatable portion 40 using the skin layer 72 while supporting the skin layer 72 and favorably maintaining the strength of the filter member 70 using the porous layer 71. In addition, since the filter member 70 and the inflatable portion 40 are formed of the same material, the filter member 70 can be easily welded to the inflatable portion 40 when the filter member 70 and the inflatable portion 40 are joined together.

Next, modifications of the embodiment will be described. Note that in description of each modification, the same reference symbol will be assigned to the same configuration as that of the embodiment, and a description of the same reference symbol assigned to the same configuration as that of the exemplary embodiment will be omitted.

Modification 1

Figure 6A:
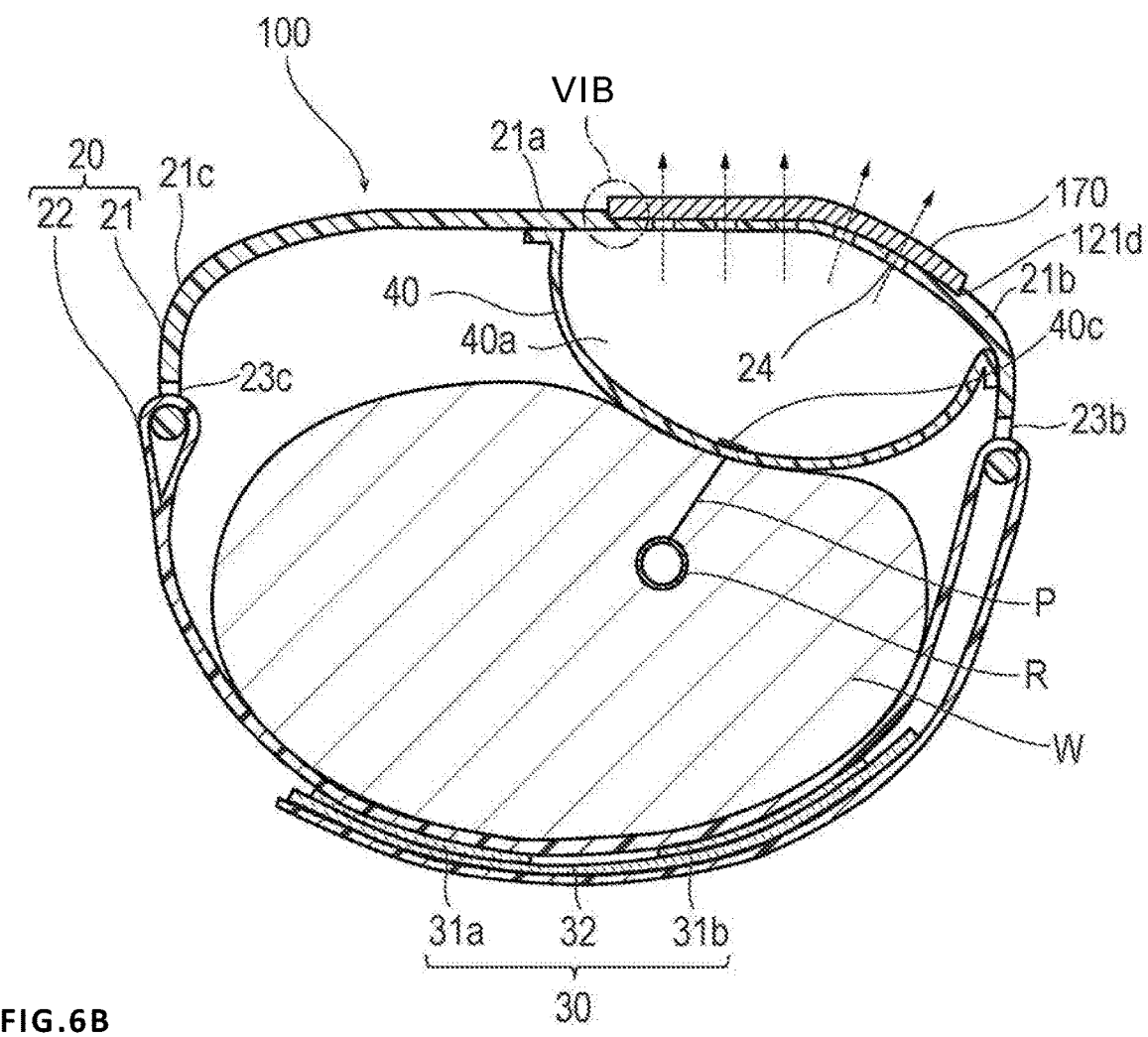
FIG. 6A is a cross-sectional view illustrating a hemostatic device according to Modification 1.
Figure 6B:
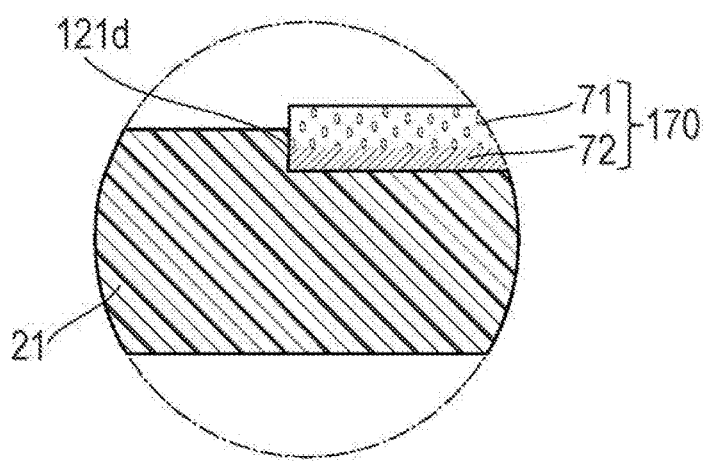
FIG. 6B is an enlarged view of part VIB of FIG. 6A.

FIGS. 6A and 6B are diagrams of a hemostatic device 100 according to Modification 1.

In the hemostatic device 100 according to Modification 1, an arrangement position of a filter member 170 is different from that of the exemplary embodiment.

Specifically, as illustrated in FIG. 6A, the filter member 170 is disposed on the outer surface side of the support plate 21 in a region in which the hole portions 24 of the support plate 21 are provided. Note that the filter member 170 has an asymmetric membrane including a porous layer 71 and a skin layer 72 similarly to the exemplary embodiment.

A depression 121d recessed from the outer surface side toward the inner surface side is formed in a region in which the filter member 170 of the support plate 21 is disposed. Further, as illustrated in FIG. 6B, the filter member 170 is disposed on the outer surface of the support plate 21 so that the skin layer 72 enters the depression 121d. For this reason, it is possible to suitably prevent the skin layer 72, which is a thin layer and liable to be damaged, from being exposed to the outside and come into contact with the wearer and/or the peripheral medical instrument, and being damaged. In addition, since a part of the filter member 170 is disposed in the depression 121d, position shift of the filter member 170 can be prevented from occurring.

As described above, according to the hemostatic device 100 according to Modification 1, the filter member 70 is disposed on the outer surface side of the band 20. For this reason, it is possible to assign a function of adjusting the discharge speed of gas to the hemostatic device 100 by disposing the filter member 70 to cover the hole portions 24 from the outer surface side of the band 20 in which the hole portions 24 are formed. Therefore, according to Modification 1, a manufacturing operation of the hemostatic device 100 becomes rather easy.

Note that even though the above Modification shows an example in which the filter member 170 is disposed in the depression 121d formed on the support plate 121, for example, the depression 121d may not be formed on the support plate 121, and the filter member 170 may be disposed on the outer surface of the support plate 121.

Modification 2

Figure 7:
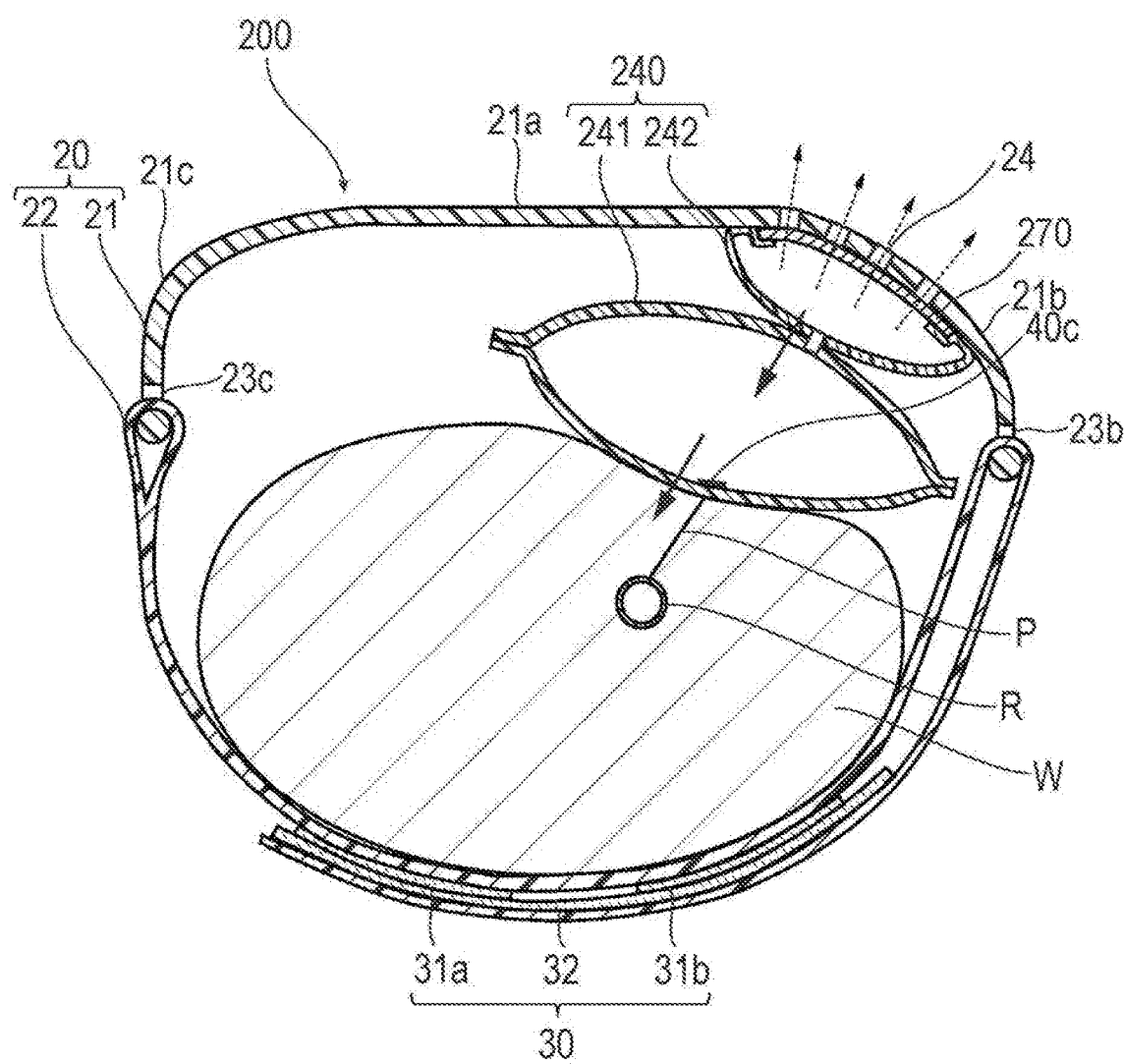
FIG. 7 is a cross-sectional view illustrating a hemostatic device according to Modification 2.

FIG. 7 is a diagram for description of a hemostatic device 200 according to Modification 2.

In the hemostatic device 200 according to Modification 2, a configuration of an inflatable portion 240 is different from that of the exemplary embodiment.

The inflatable portion 240 includes a first pressing portion 241 that presses the puncture site P and a second pressing portion 242 disposed between the first pressing portion 241 and the support plate 21 to adjust a direction of a pressing force applied by a pressing force of the first pressing portion 241 to a direction toward the puncture site P.

The first pressing portion 241 is formed by overlapping two substantially rectangular sheets to form a bag shape. Similarly, to the inflatable portion 40, the injection part 60 is connected to the first pressing portion 241 (not illustrated). Note that a configuration of the first pressing portion 241 is not particularly limited as long as the first pressing portion 241 is inflatable by being injected with gas. For example, the first pressing portion 241 may be configured by a bag-shaped member obtained by folding one sheet and joining edge portions, or configured by a balloon-shaped member not having an edge portion. In addition, an external shape of the first pressing portion 241 is not particularly limited. For example, the first pressing portion 241 may have an external shape such as a circle, an ellipse, or a polygon in plan view.

The second pressing portion 242 can include a substantially rectangular sheet. The second pressing portion 242 is disposed to cover a region in which the hole portions 24 are provided on the inner surface side of the support plate 21. An outer peripheral edge portion of the second pressing portion 242 is joined to the support plate 21 and the outer peripheral edge portion of the filter member 70 in a state of being tucked (or placed) in to the support plate 21 side. A space into which gas is injected is formed between the second pressing portion 242 and the filter member 70. A substantially central portion of the second pressing portion 242 is connected to the first pressing portion 241, and an internal space of the first pressing portion 241 and an internal space of the second pressing portion 242 communicate with each other.

The marker 40c is provided at a substantially central portion of an inner surface of the first pressing portion 241.

As described above, according to the hemostatic device 200 of Modification 2, a direction of a pressing force applied by the first pressing portion 241 may be adjusted to a direction toward the puncture site P as indicated by a solid arrow in FIG. 7 using the second pressing portion 242.

Modification 3

Figure 8A:
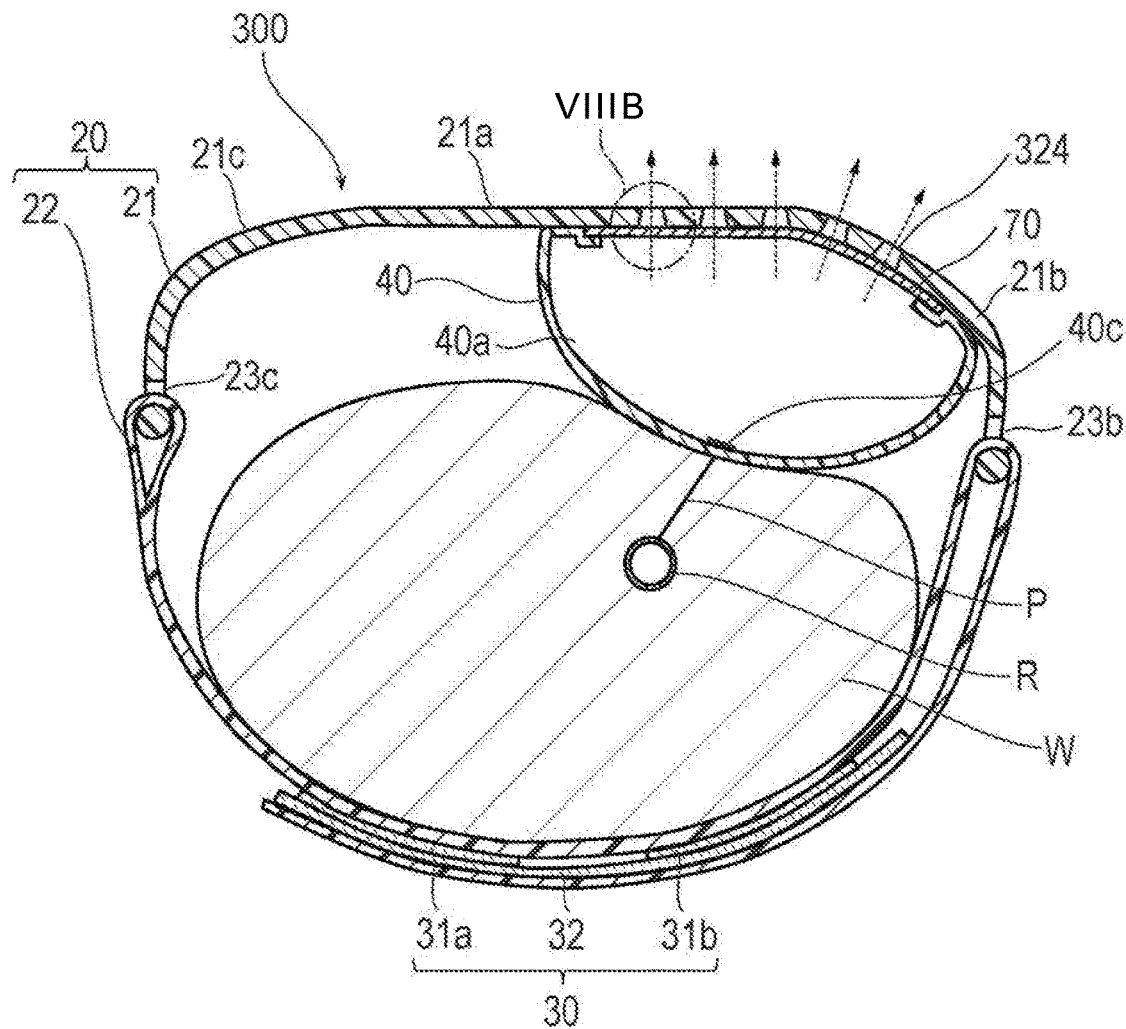
FIG. 8A is a cross-sectional view illustrating a hemostatic device according to Modification 3.
Figure 8B:
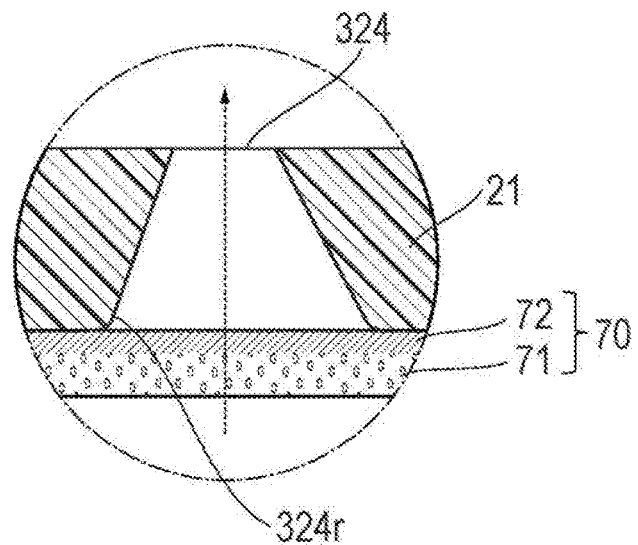
FIG. 8B is an enlarged view of part VIIIB of FIG. 8A.

FIGS. 8A and 8B are diagrams of a hemostatic device 300 according to Modification 3.

In the hemostatic device 300 according to Modification 3, a shape of a hole portion 324 provided in the support plate 21 is different from that of the embodiment.

As illustrated in FIG. 8B, in a cross section along the thickness direction of the support plate 21, the hole portion 324 has a tapered shape from the inner surface side to the outer surface side of the support plate 21. For this reason, while favorably maintaining gas permeability by keeping a contact area between the filter member 70 and the hole portion 324 relatively large, it is possible to suitably inhibit foreign matter from entering the hole portion 324 from the outer surface side to damage the filter member 70.

In addition, a corner portion 324r on the inner surface side of the support plate 21 forming the hole portion 324 has a rounded shape. For this reason, the filter member 70 can be prevented from being damaged when the filter member 70 comes into contact with the corner portion 324r.

Note that a shape of the hole portion 324 in plan view from the inner surface side of the support plate 21 is not particularly limited, and may correspond to, for example, a polygonal shape such as a regular hexagon, a circular shape, or an elliptical shape.

Modification 4

Figure 9:
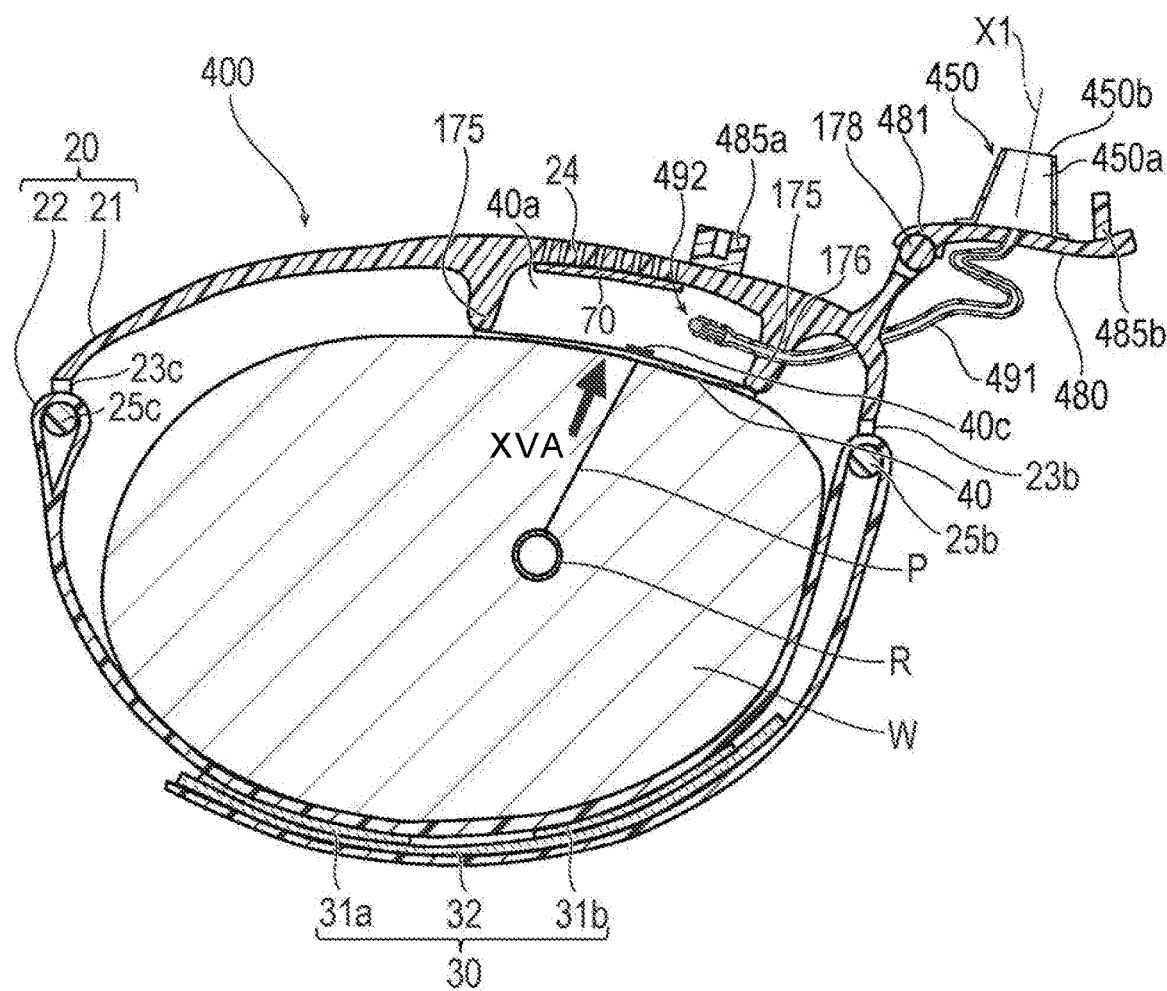
FIG. 9 is a cross-sectional view illustrating a hemostatic device according to Modification 4.
Figure 10:
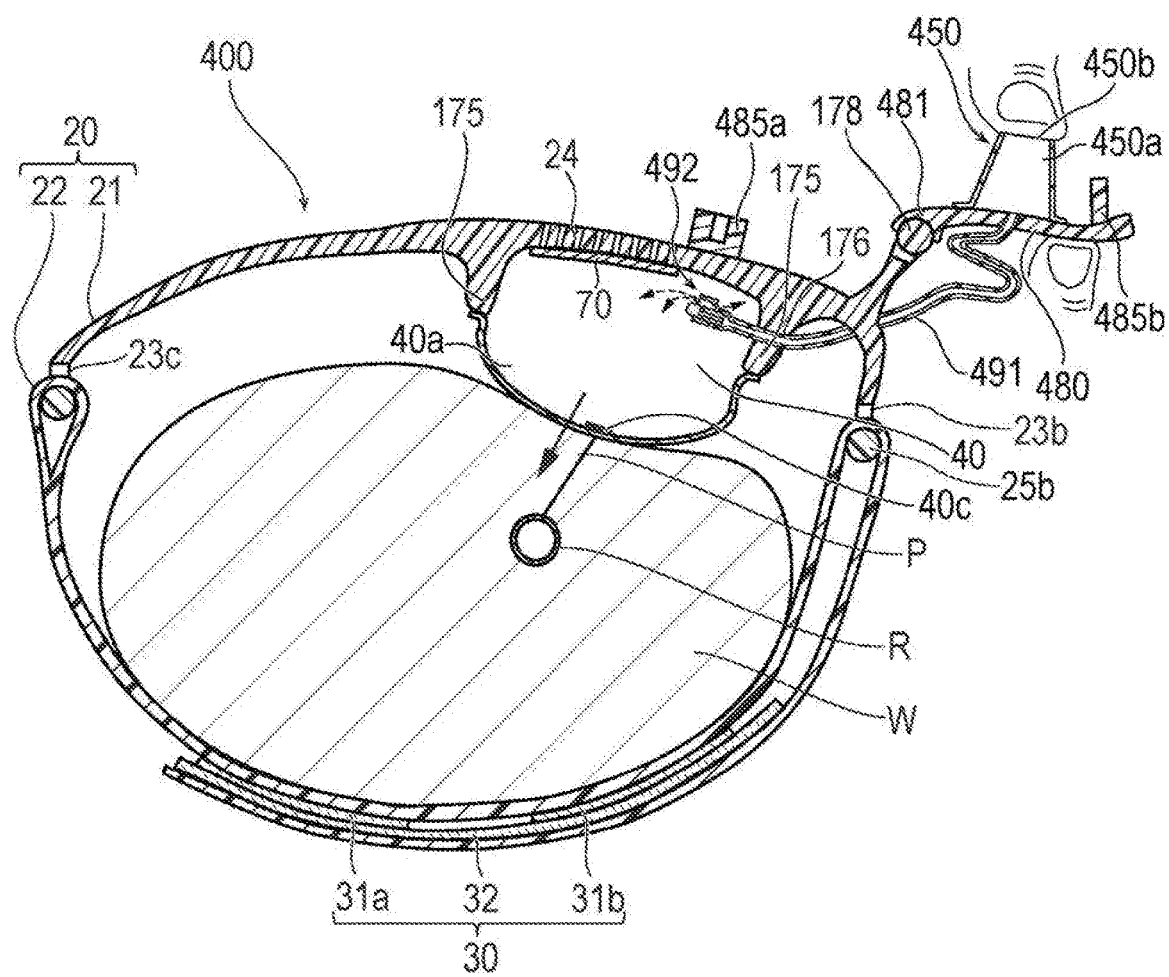
FIG. 10 is a cross-sectional view illustrating the hemostatic device according to Modification 4.
Figure 11:
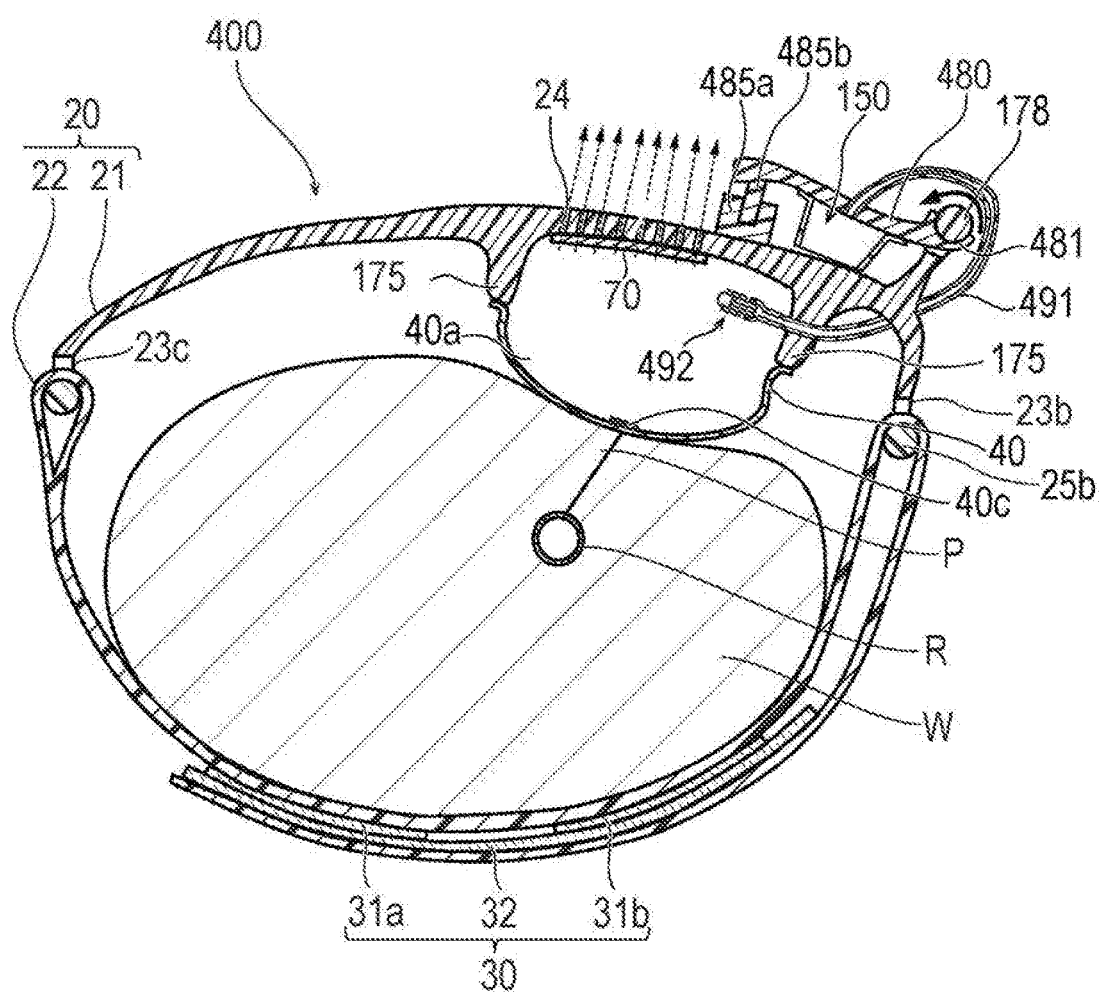
FIG. 11 is a cross-sectional view illustrating the hemostatic device according to Modification 4.
Figure 13:
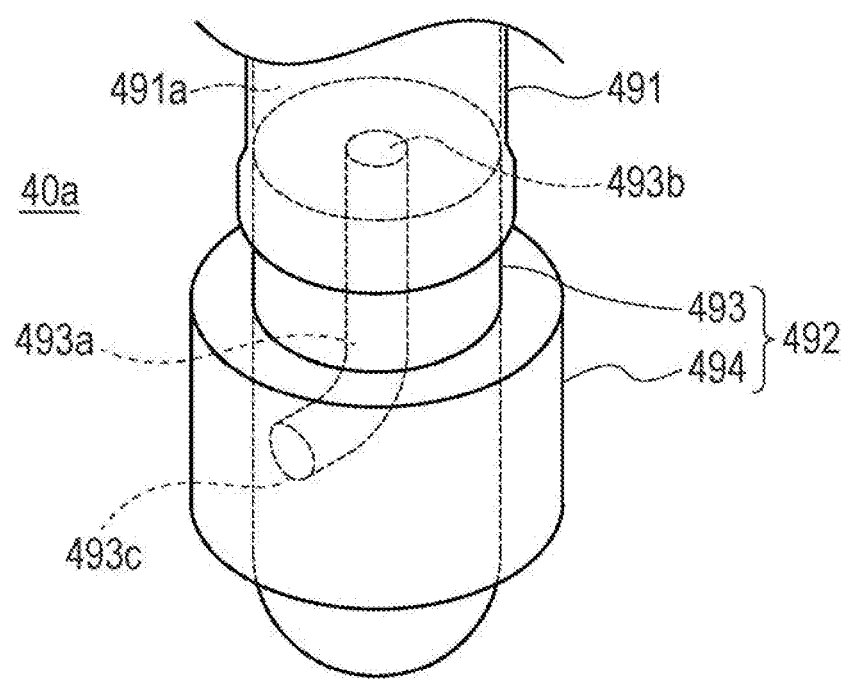
FIG. 13 is a schematic perspective view illustrating a backflow check structure of the hemostatic device according to Modification 4.
Figure 14A:
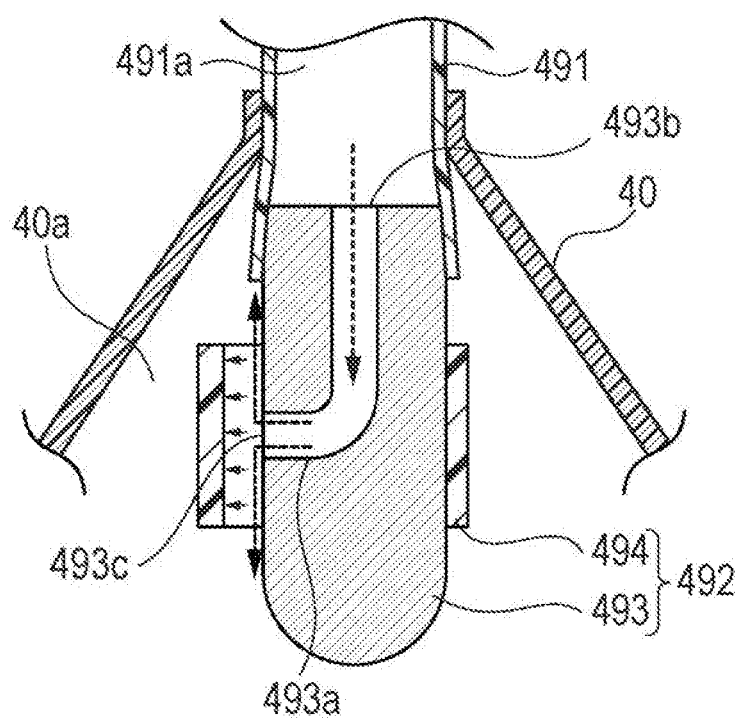
Figure 14B:
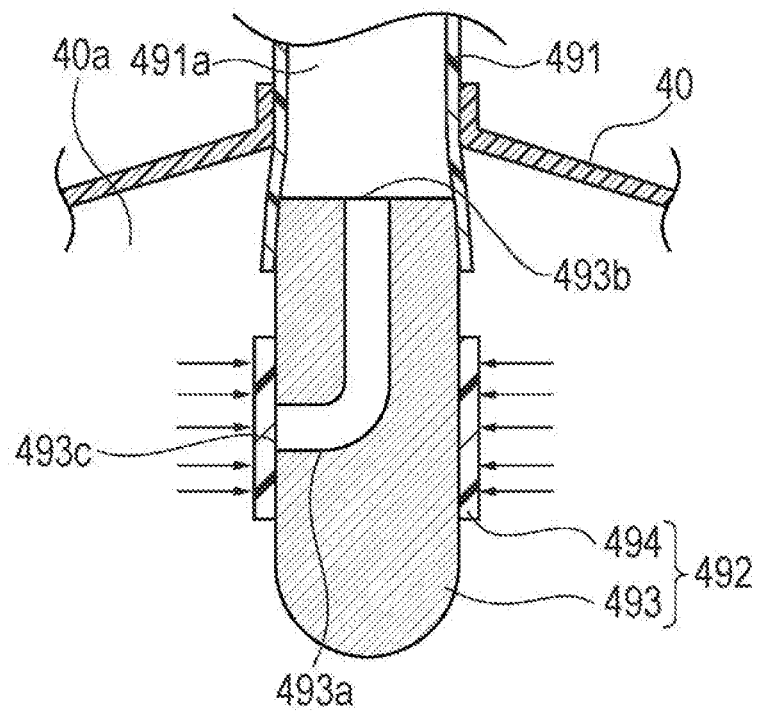
FIG. 14B is a diagram illustrating a state in which inflation of the inflatable portion is completed.
Figure 15:
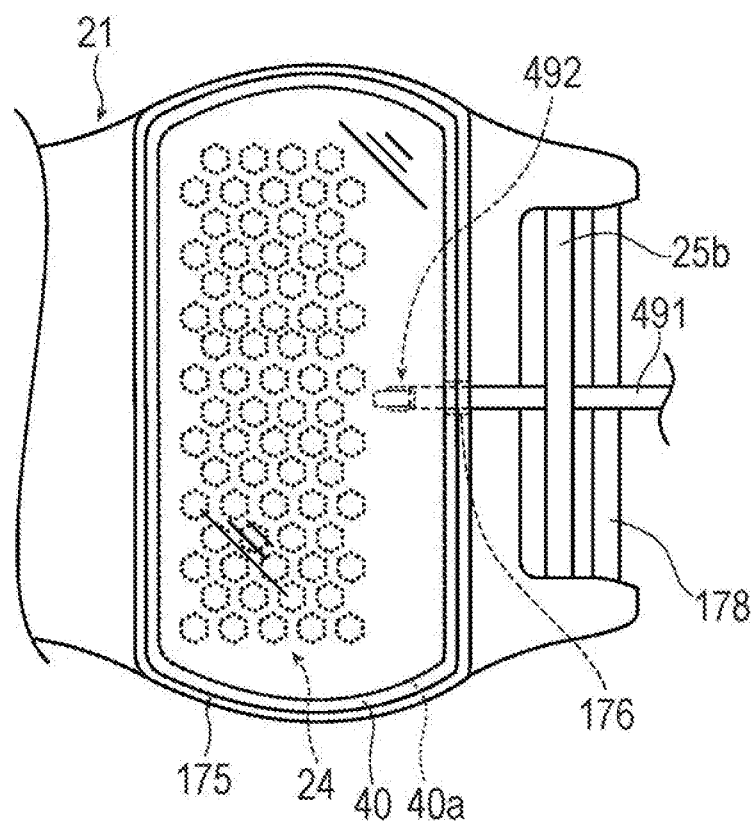
FIG. 15 is a plan view of a support plate viewed in a direction of an arrow XVA illustrated in FIG. 9.

FIGS. 9 to 15 are diagrams of a hemostatic device 400 according to Modification 4. FIGS. 9 to 11 are cross-sectional views illustrating a state in which the hemostatic device 400 is mounted, FIGS. 12 to 14B are diagrams illustrating an injection part 450 and a backflow check structure 492, and FIG. 15 is a diagram illustrating the support plate 21 (support body portion) included in the hemostatic device 400.

As illustrated in FIG. 9, in the hemostatic device 400 according to Modification 4, the injection part 450 is configured to inject gas (for example, air) into the inflatable portion 40 is integrally provided on the hemostatic device 400.

Figure 12:
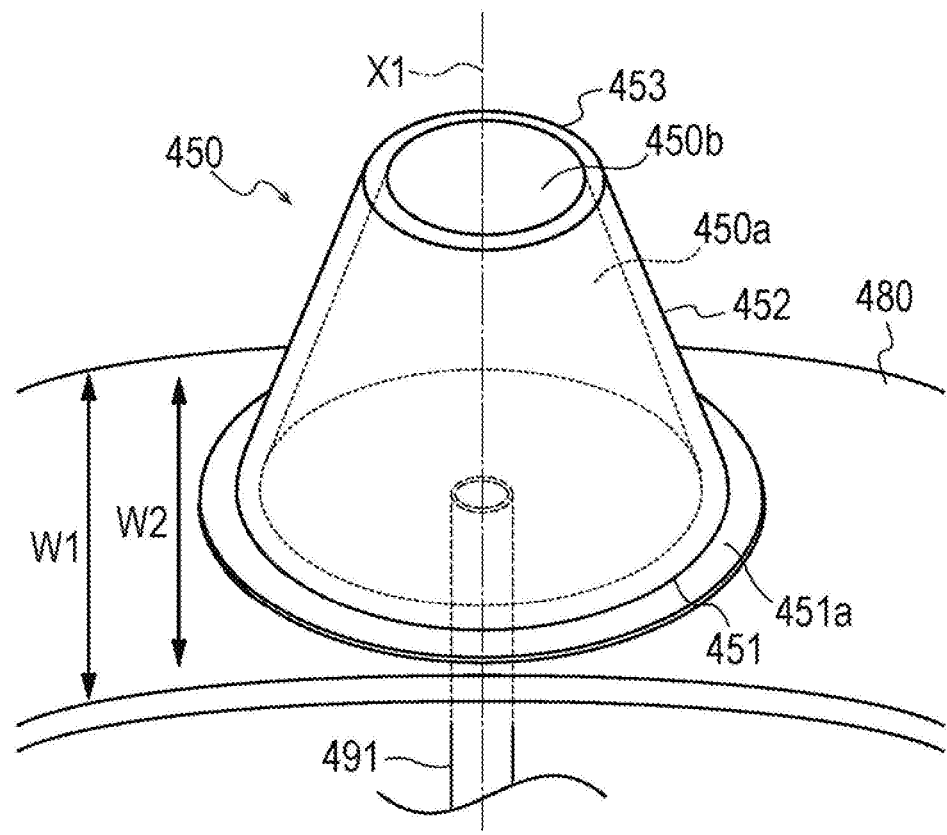
FIG. 12 is a schematic perspective view illustrating an injection part of the hemostatic device according to Modification 4.

As illustrated in FIG. 12, the injection part 450 is configured by a three-dimensional (3D) member including a housing space (lumen) 450a capable of housing gas (air). The injection part 450 is configured to be elastically transformable, and injects air into the inflatable portion 40 by being elastically transformed.

As illustrated in FIGS. 9-12, the injection part 450 has a hole portion 450b penetrating the injection part 450 and communicating with the housing space 450a. The hole portion 450b is disposed on a perpendicular line X1 with respect to a region of a holding plate 480 described below in which the injection part 450 is disposed.

As illustrated in FIG. 12, the injection part 450 has a bottom part 451 secured to the holding plate 480, a vertical wall part 452 projecting from the bottom part 451 toward the hole portion 450b, and an upper part 453 including the hole portion 450b. The bottom part 451 is provided with a securing portion 451a secured with the injection part 450 on the holding plate 480. For example, the injection part 450 is secured to the holding plate 480, for example, by an adhesive.

In the present embodiment, the bottom part 451 of the injection part 450 is formed by an opening facing an outer surface of the holding plate 480. For this reason, the bottom part 451 is not included in a bottom face of the injection part 450, and a part of the outer surface of the holding plate 480 is included in the bottom face of the injection part 450. The housing space 450a of the injection part 450 corresponds to a space surrounded by the part of the outer surface of the holding plate 480 and the vertical wall part 452.

An outer periphery of the vertical wall part 452 is formed to become smaller from the bottom part 451 side to the hole portion 450b side (a direction away from the bottom part 451). In addition, as illustrated in FIGS. 9-12, the vertical wall part 452 is formed in a tapered shape in a cross section parallel to the perpendicular line X1 with respect to the region of the holding plate 480 in which the injection part 450 is disposed. In accordance with an exemplary embodiment, the tapered shape is a shape in which an outer peripheral length gradually decreases from the bottom part 451 toward the hole portion 450b.

Note that an external shape of the injection part 450 is not particularly limited and may correspond to, for example, a polygonal prism such as a quadrangular prism, a sphere having no distinction between the bottom part, the vertical wall part, and the upper part, a shape other than a tapered shape in section view. In addition, even though the injection part 450 in which the bottom part 451 and the upper part 453 include openings (hole portions) is illustrated, the injection part 450 may have a structure in which a bottom face is formed in the bottom part and an upper face is formed in the upper part. In addition, the number of hole portions 450b is not particularly limited as long as the number is one or more, and a shape of the hole portion 450b is not limited to the illustrated shape.

The volume of the housing space 450a of the injection part 450 is preferably about ¼ to ⅓ of the volume of the inflatable space 40a of the inflatable portion 40. In this way, the injection part 450 is formed to an appropriate size to prevent the injection part 450 from hindering manipulation performed around the hemostatic device 10, and it is possible to reduce the number of times of performing an injection operation of injecting air into the inflatable portion 40 described below.

For example, the injection part 450 is preferably made of an elastomer material such as silicone rubber or latex rubber, a thermoplastic plastic material such as polypropylene or polyethylene, or various thermoplastic elastomer materials having both properties of these materials so that the injection part 450 is contractible and can be restored to an original shape after contraction. Note that it is preferable that the injection part 450 is formed to be relatively thin so that the injection part 450 can be folded in a vertical direction (vertical direction of FIG. 12) when the holding plate 480 is secured to the support plate 21 as described below (see FIG. 11).

As illustrated in FIG. 9, the housing space 450a of the injection part 450 communicates with the inflatable space 40a of the inflatable portion 40 through a tube 491.

In accordance with an exemplary embodiment, the injection part 450 obtains an initial shape illustrated in FIG. 9 by taking air into the housing space 450a from the hole portion 450b. When an operation of inflating the inflatable portion 40 using the injection part 450 is performed, the injection part 450 is transformed to be deformed while blocking the hole portion 450b using a finger as illustrated in FIG. 10 in a state in which the injection part 450 has the initial shape.

When an operation of deforming the injection part 450 is performed as described above, air is sent or directed to the inflatable portion 40 via the tube 491. When an operation of sending air to the inflatable portion 40 is performed again, the finger is moved from the hole portion 450b so that the housing space 450a communicates with the outside. The injection part 450 is transformed to be restored to the initial shape illustrated in FIG. 9 by air taken into the housing space 450a from the hole portion 450b. When the injection part 450 is squeezed again in a state in which air is taken into the housing space 450a, air may be sent (i.e., directed) to the inflatable portion 40.

As illustrated in FIGS. 9-12, the injection part 450 is disposed on the holding plate 480. The holding plate 480 is connected to the support plate 21.

The holding plate 480 has a second connecting portion 481 connectable to a first connecting portion 178 of the support plate 21.

The first connecting portion 178 of the support plate 21 includes a shaft-shaped member having a substantially circular cross-sectional shape. The second connecting portion 481 of the holding plate 480 includes a recessed groove that can be fit to the first connecting portion 178 of the support plate 21. As illustrated in FIG. 11, the second connecting portion 481 of the holding plate 480 is rotatable along an outer peripheral surface of the first connecting portion 178 in a state of being fit to the first connecting portion 178 of the support plate 21.

As illustrated in FIG. 11, the first connecting portion 178 of the support plate 21 is integrally formed with the support plate 21 and protrudes in a direction away from the outer surface of the support plate 21. A gap portion is provided in a peripheral portion of the first connecting portion 178. The gap portion helps prevent the holding plate 480 and the support plate 21 from interfering with each other when the holding plate 480 rotates, thereby enabling the holding plate 480 to rotate relatively smoothly. In this way, the holding plate 480 is configured to be rotatable around the first connecting portion 178 (rotating shaft) that intersects a longitudinal direction of the band 20. Note that it is preferable that the holding plate 480 is configured to be rotatable around the first connecting portion 178 (rotating shaft) orthogonal to the longitudinal direction of the band 20. In this way, the injection part 450 and the holding plate 480 are less liable to protrude toward the wrist W side of the support plate 21 when the holding plate 480 rotates.

For example, the holding plate 480 may be made of the same material as that of the support plate 21. Note that it is preferable that the holding plate 480 is made of a material more rigid than that of the injection part 450. In this way, the operator can easily grip the injection part 450 when air is sent to the inflatable portion 40 described below.

As illustrated in FIG. 12, a width W1 of the holding plate 480 is formed to be longer than a width W2 of the injection part 450. Note that the width means a dimension (see FIG. 1) along a direction orthogonal to the longitudinal direction of the band 20. In addition, the width of the injection part 450 means a width dimension of a portion having a largest width direction in the injection part 450, and refers to a width of the securing portion 451*a* in the present modification.

When the width W2 of the injection part 450 is formed to be smaller than the width W1 of the holding plate 480, the injection part 450 does not protrude in a width direction of the holding plate 480. For this reason, in a state in which the hemostatic device 400 is mounted on the wrist W (see FIG. 4), the injection part 450 does not protrude to the wrist W side. In this way, the injection part 450 rarely comes into contact with the wrist W of the wearer, and thus it is possible to reduce discomfort felt by the wearer.

In addition, for example, the width W1 of the holding plate 480 may be formed to be smaller than a width of the support plate 21. When the width W1 of the holding plate 480 is formed to be smaller than the width of the support plate 21, the width W2 of the injection part 450 is formed to be smaller than the support plate 21. In this way, the holding plate 480 and the injection part 450 are more reliably prevented from protruding to the wrist W side of the support plate 21, and thus it is possible to suitably reduce discomfort felt by the wearer.

Note that a configuration of the holding plate 480 is not particularly limited as long as the injection part 450 can be disposed. For example, a dimension and a cross-sectional shape of each portion can be appropriately changed.

A lock mechanism for securing the holding plate 480 is provided on the support plate 21 and the holding plate 480. The lock mechanism includes a first member 485*a* provided on the support plate 21 and a second member 485*b* provided on the holding plate 480.

The first member 485*a* has a depression into which the second member 485*b* can be fit. As illustrated in FIG. 11, when the holding plate 480 rotates, the second member 485*b* fits into the depression of the first member 485*a*, thereby securing the holding plate 480 to the support plate 21. In this way, rotation of the holding plate 480 can be restricted. For example, when the holding plate 480 is secured after the inflatable portion 40 is inflated using the injection part 450, it is possible to prevent the injection part 450 provided on the holding plate 480 from inadvertently rotating. For this reason, when the hemostatic device 400 is operated after the inflatable portion 40 is inflated, it is possible to prevent a smoother operation from being hindered by the injection part 450. In addition, when the holding plate 480 is secured to the support plate 21, the injection part 450 is interposed between the holding plate 480 and the support plate 21. For this reason, the hemostatic device 400 can help prevent the injection part 450 from being unexpectedly deformed (or damaged) when air is sent (or directed) into the inflatable portion 40.

Note that a configuration of the lock mechanism is not particularly limited as long as rotation of the holding plate 480 can be restricted. The lock mechanism is not limited to a structure for restricting rotation of the holding plate 480 by mechanical connection (fitting) between members, and may correspond to, for example, a structure for restricting rotation of the holding plate 480 by, for example, a magnetic force. In addition, in a case of having a structure for securing the holding plate 480 by mechanical connection, a specific shape, a position, and a size of the lock mechanism (the first member 485*a* and the second member 485*b*), and the number of lock mechanisms are not particularly limited to illustrated ones.

As illustrated in FIG. 12, the injection part 450 extends in a direction away from the outer surface of the holding plate 480, and the hole portion 450*b* is disposed on the perpendicular line X1 with respect to the region of the holding plate 480 in which the injection part 450 is disposed. For this reason, a direction in which the injection part 450 is pressed when air is injected into the inflatable portion 40 corresponds to a direction (vertical direction) along the perpendicular line X1 with respect to the region of the holding plate 480 in which the injection part 450 is disposed (see FIG. 10). For this reason, it is possible to efficiently apply a force to the injection part 450 from the finger, and to smoothly inject air into the inflatable portion 40. Note that when the injection part 450 is deformed, as illustrated in FIG. 10, the injection part 450 may be efficiently deformed by interposing the injection part 450 between two fingers from the outer surface side and the inner surface side of the holding plate 480.

Since the outer periphery of the vertical wall part 452 becomes smaller from the bottom part 451 side toward the hole portion 450*b* side, when the operation of deforming the injection part 450 is performed, the injection part 450 rarely buckles on the bottom part 451 side, and it is possible to prevent damage such as folding from occurring. Further, since the outer periphery of the vertical wall part 452 becomes smaller from the bottom part 451 side toward the hole portion 450*b* side, when the operation of deforming the injection part 450 is performed, the injection part 450 is transformed such that the hole portion 450*b* side of the injection part 450 is folded to the inside of the housing space 50*a* of the injection part 450. For this reason, it is possible to deform the injection part 450 from the hole portion 450*b* side toward the bottom part 451 side with a small force, and to efficiently send (or direct) air into the housing space 450*a* to the inflatable portion 40.

Since the injection part 450 is secured to the relatively rigid holding plate 480, when the injection part 450 is pressed, it is possible to prevent the holding plate 480 from being transformed. In addition, since the holding plate 480 is rotatably connected to the support plate 21, a pressing force transmitted to the holding plate 480 at the time of pressing the injection part 450 is absorbed by a connecting part between the holding plate 480 and the support plate 21. As a result, a pressing force generated when the injection part 450 is pressed is difficult to be transmitted to the support plate 21 and is difficult to be transmitted to the puncture site P. For this reason, the wearer can appropriately detect only a pressing force applied to the puncture site P from the inflatable portion 40 while an operation of inflating the inflatable portion 40 is performed. Therefore, when the injection part 450 is operated based on a pressing force felt by the wearer, an optimum (i.e., desired) amount of air for hemostasis in the puncture site P can be injected into the inflatable portion 40.

As illustrated in FIGS. 12 and 13, a proximal portion of the tube 491 is attached to the bottom part 451 side of the injection part 450, and a distal portion of the tube 491 is disposed in the inflatable space 40a of the inflatable portion 40. Note that a position of the injection part 450 at which the tube 491 is attached is not particularly limited as long as the housing space 450a of the injection part 450 and the inflatable space 40a of the inflatable portion 40 can communicate with each other. For example, the proximal portion of the tube 491 may be attached to the vertical wall part 452 of the injection part 450. However, when the hole portion 450b is disposed on the upper part 453 side as in the present embodiment, the proximal portion of the tube 491 is preferably attached to the bottom part 451 side of the injection part 450 to efficiently send air in the housing space 450a to the inflatable portion 40.

FIG. 15 illustrates the plan view of the support plate 21 viewed in the direction of the arrow XVA illustrated in FIG. 9 (plan view viewed from the inner surface side of the support plate 21) in a simplified manner.

A protrusion 175 surrounding a periphery of the plurality of hole portions 24 is formed on the support plate 21.

As illustrated in FIG. 10, the inflatable portion 40 is secured to the protrusion 175. The inflatable portion 40 is secured to the protrusion 175, thereby forming the inflatable space 40a having airtightness in a space surrounded by the protrusion 175 and the inflatable portion 40. The protrusion 175 is formed to surround the periphery of the plurality of hole portions 24 and protrude from the inner surface of the support plate 21. Note that it is preferable that the protrusion 175 is formed to surround the entire periphery of the plurality of hole portions 24. In this way, it is possible to rather easily secure the inflatable portion 40 to the protrusion 175, and to rather easily attach the inflatable portion 40 to the support plate 21. In addition, it is sufficient that the inflatable portion 40 is secured to form the inflatable space 40a between the inflatable portion 40 and the protrusion 175, and may be secured to, for example, a portion other than an end portion of the protrusion 175 in a protruding direction. In addition, the protrusion 175 may not be formed to surround the entire periphery of the plurality of hole portions 24. In this case, the inflatable space 40a is formed by a space surrounded by the support plate 21, the inflatable portion 40, and the protrusion 175.

The protrusion 175 formed on the support plate 21 has a function of adjusting a distance between the puncture site P and the support plate 21 in a state in which the hemostatic device 10 is mounted on the wrist W and before the inflatable portion 40 is inflated (state illustrated in FIG. 9).

When the support plate 21 is disposed on the wrist W at the time of wrapping the band 20 around the wrist W, the protrusion 175 comes into contact with the wrist W. The distance between the puncture site P and the support plate 21 is adjusted to a predetermined size according to a height dimension (a dimension in the protruding direction) of the protrusion 175. For this reason, for example, a distance between the inflatable portion 40 and the puncture site P before inflation is started may be kept at a predetermined distance irrespective of a difference in outer peripheral length of the wrist W for each wearer. Further, when inflation is performed in a state in which the distance between the inflatable portion 40 and the puncture site P before inflation is started is adjusted to the predetermined distance, it is possible to apply a constant pressing force regardless of the outer peripheral length of the wrist W of the wearer.

As illustrated in FIG. 9, for example, the protrusion 175 may be formed in a cross-sectional shape in which a distal portion in the protruding direction is rounded. The protrusion 175 helps prevent an excessive pressing force from being applied to the wearer at the time of coming into contact with the wrist W by having such a cross-sectional shape.

The height dimension (the dimension in the protruding direction), the cross-sectional shape, and a position disposed on the support plate 21 of the protrusion 175 are not particularly limited, and may be appropriately changed. In addition, the protrusion 175 may be formed integrally with the support plate 21 and may be formed as a member separate from the support plate 21. In addition, a cushioning member for alleviating a pressing force at the time of coming into contact with a skin may be provided on the protrusion 175.

As illustrated in FIG. 9, a through-hole is provided in the holding plate 480, and the proximal portion of the tube 491 is disposed to be inserted into the through-hole. In addition, as illustrated in FIG. 15, a through-hole 176 into which a part of the tube 491 is inserted is provided in the protrusion 175 of the support plate 21.

As illustrated in FIGS. 9 and 15, for example, the tube 491 can communicate with the inflatable portion 40 through the through-hole of the holding plate 480, an inner surface side of the first connecting portion 178 of the support plate 21, an outer surface side of a connecting end portion 25b to which the band 20 is connected in the support plate 21, and the through-hole 176 formed in the support plate 21.

The tube 491 has a deflection portion having a predetermined length before rotation of the holding plate 480 (see FIG. 9). As illustrated in FIG. 11, the deflection portion of the tube 491 is extended to release a deflected state when the holding plate 480 is rotated. When the deflection portion is extended, it is possible to prevent rotation of the holding plate 480 from being obstructed by the tube 491. In addition, the part of the tube 491 inserted into the through-hole 176 of the support plate 21 is secured to the support plate 21 so that position shift does not occur in the tube 491 due to rotation of the holding plate 480. For example, securing may be performed using an adhesive.

As illustrated in FIG. 9, the backflow check structure 492 for preventing backflow from the inside of the inflatable space 40a to the injection part 450 side is provided at the distal portion of the tube 491 disposed inside the inflatable space 40a.

The backflow check structure 492 is disposed inside the inflatable portion 40. As illustrated in FIGS. 13, 14A and 14B, the backflow check structure 492 includes a core material 493 connected to the distal portion of the tube 491 and a covering member 494 covering the core material 493.

The core material 493 is connected to the tube 491 by inserting and securing a proximal portion of the core material 493 into a distal side of a lumen 491a of the tube 491.

The core material 493 has a substantially columnar external shape. The core material 493 includes a proximal end opening 493b that opens inside the lumen 491a of the tube 491, a distal end opening 493c that opens on a surface on which the covering member 494 is provided in the core material 493, and a lumen 493a that communicates with the proximal end opening 493b and the distal end opening 493c.

Note that the core material 493 may be connected to the tube 491 in a mode other than a scheme of inserting and securing the proximal portion of the core material 493 into the lumen 491a of the tube 491. For example, each of a distal end surface of the core material 493 and a proximal end surface of the tube 491 may be secured in a butted state, and the lumen 493a of the core material 493 and the lumen 491a of the tube 491 may be allowed to air-tightly communicate with each other.

The material of the core material 493 preferably corresponds to a material having rigidity greater than that of the material of the covering member 494. Examples of the material of the core material 493 can include a known metal material, and/or a plastic material.

The covering member 494 has a cylindrical external shape. The core material 493 is inserted into the covering member 494.

The covering member 494 material preferably corresponds to an elastic member. Examples of the material of the covering member 494 can include an elastomer material such as butyl rubber, polysulfide rubber, epichlorohydrin rubber, high nitrile rubber, fluororubber, or silicone rubber, and various thermoplastic elastomer materials.

An operation of the backflow check structure 492 will be described with reference to FIGS. 14A and 14B. In FIGS. 14A and 14B, a dotted arrow indicates a flow of air, and a solid arrow indicates a direction of a pressure applied to the covering member 494 by air.

As illustrated in FIG. 14A, when air is injected into the tube 491 from the injection part 450 in a state in which the inflatable portion 40 is insufficiently inflated, air passes through the lumen 493a of the core material 493 to apply a pressure in a direction away from the core material 493 to the covering member 494.

When a pressure received from air sent from the injection part 450 is greater than or equal to a predetermined magnitude, the covering member 494 is separated from an outer surface of the core material 493 to allow communication between the distal end opening 493c and the inflatable space 40a. For example, when an operation of sufficiently deforming the injection part 450 is not performed, and the amount of air sent from the injection part 450 side is small, the pressure applied to the covering member 494 decreases, and thus it is impossible to allow communication between the distal end opening 493c and the inflatable space 40a. On the other hand, when the injection part 450 is slowly pressed for a relatively long time, and the operation of sufficiently deforming the injection part 450 is performed, the covering member 494 is separated from the outer surface of the core material 493. Even in a case in which the hole portion 450b of the injection part 450 is erroneously closed by an article, when the operation of sufficiently deforming the injection part 450 is not performed, air is not inadvertently sent into the inflatable portion 40, and thus it is possible to suitably prevent the puncture site P from being pressed more than necessary.

As illustrated in FIG. 14B, in a state in which the inflatable portion 40 is sufficiently inflated, air in the inflatable portion 40 applies a pressure in a direction of coming into contact with the core material 493 to the covering member 494. In this way, the distal end opening 493c is blocked by the covering member 494, and thus the air in the inflatable portion 40 does not flow back to the core material 493 side, consequently to the injection part 450 side. In addition, in the state in which the inflatable portion 40 is sufficiently inflated, the air in the inflatable portion 40 applies a pressure to the covering member 494 to block the distal end opening 493c. The pressure is higher than an injection pressure of air. For this reason, when the inflatable portion 40 is sufficiently inflated, and the internal pressure of the inflatable portion 40 becomes a predetermined value, air may not be injected from the injection part 450 into the inflatable portion 40. In this way, in the state in which the inflatable portion 40 is sufficiently inflated, it is possibly suitably prevent air from being injected into the inflatable portion 40 more than necessary to excessively inflate the inflatable portion 40, thereby pressing the puncture site P more than necessary.

When a hemostasis treatment is performed using the hemostatic device 400 according to the present modification, as illustrated in FIG. 11, discharge of gas injected into the inflatable portion 40 is performed mainly through the hole portions 24 provided in the band 20 and the filter member 70. For this reason, it is unnecessary to make the thickness of the inflatable portion 40 relatively thin to increase the gas permeation amount, and it is possible to favorably keep the strength of the inflatable portion 40. In addition, to control discharge of the gas injected into the inflatable portion 40, the filter member 70 may suppress discharge of the gas when compared to a case in which the gas is discharged from the hole portions 24 provided in the band 20 (a case in which the hole portions 24 are not blocked by the filter member 70). That is, the discharge speed of the gas injected into the inflatable portion 40 may be rather easily and precisely adjusted by the filter member 70.

In addition, the hemostatic device 400 has the injection part 450 integrally provided with the hemostatic device 400. For this reason, inflation of the inflatable portion 40 may be performed by a simple operation without using a dedicated instrument separate from the hemostatic device 400.

Note that in the hemostatic device 400 of Modification 4, a position at which the filter member 70 is disposed is not limited to the inner surface side of the support plate 21, and may correspond to the outer surface side of the support plate 21. In addition, the second pressing portion 242 (see FIG. 7) shown in Modification 2 may be provided in the hemostatic device 400. In addition, the injection part 450 may be disposed on the support plate 21 without being disposed on the holding plate 480 connected to the support plate 21. In addition, the holding plate 480 may include a part of the support plate 21. In this case, to allow the holding plate 480 to be rotatable, for example, a hinge portion, a part of which is made thin, may be provided on the support plate 21.

Even though the hemostatic device according to the invention has been described above through the embodiment and modifications, the invention is not limited only to the respective configurations described above, and can be appropriately changed based on the description of claims.

For example, each portion included in the hemostatic device may be replaced with a portion having an arbitrary configuration capable of exerting the same function. In addition, an arbitrary component may be added.

In addition, the invention is not limited to the hemostatic device used by being mounted on the wrist, and may be applied to a hemostatic device used by being mounted, for example, on a leg.

In addition, in the embodiment, a description has been given of a case in which the inflatable portion and the filter member are made of the same material. However, materials of the inflatable portion and the filter member may be different from each other.

In addition, in the disclosure, it is sufficient that the filter member may control discharge of gas injected into the inflatable portion, and the filter member may not include an asymmetric membrane. For example, a thermosetting elastomer such as silicone or natural rubber having high gas permeability can be used for the filter member. In addition, for the filter member, a thermoplastic resin such as polyvinyl chloride, polyethylene, polypropylene, or polyvinylidene chloride or various thermoplastic elastomers such as an olefinic thermoplastic elastomer and a styrene thermoplastic elastomer making the thickness of the filter member thin and increasing the gas permeation amount per unit area can be used. In these cases, the gas permeation amount per unit area of the filter member can be set to be larger than the gas permeation amount per unit area of the inflatable portion, and to allow discharge of gas injected into the inflatable portion to be controlled by the filter member.

In addition, in the embodiment, a description has been given of a mode in which the inflatable portion is joined to both the support plate and the filter member. However, the inflatable portion may be joined only to the support plate.

The detailed description above describes a hemostatic device for performing hemostasis by pressing a punctured site. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:
   a band configured to be wrapped around a puncture site where bleeding is to be stopped, the band having one or more hole portions penetrating between an inner surface and an outer surface of the band;
   a fastener configured to secure the band to a limb in a wrapped state;
   an inflatable portion configured to be connected to the band and inflated with a gas, the inflatable portion being disposed to cover the one or more hole portions on the inner surface of the band;
   a filter member disposed on the band to block the one or more hole portions and configured to control discharge of the gas from the inflatable portion through the one or more hole portions; and
   wherein the filter member and the inflatable portion are formed of a same material, and the filter member includes a porous layer and a skin layer having a smaller gas permeation amount per unit area than a gas permeation amount per unit area of the porous layer.

2. The hemostatic device according to claim 1, wherein the band includes a support plate on which the inflatable portion is disposed and a belt on which the fastener is disposed, and wherein the support plate has a higher elastic modulus than an elastic modulus of the inflatable portion and an elastic modulus of the belt.

3. The hemostatic device according to claim 2, wherein the filter member is disposed on an outer surface side of the support plate.

4. The hemostatic device according to claim 1, wherein the filter member is disposed between the inflatable portion and the band.

5. The hemostatic device according to claim 4, wherein an outer peripheral edge portion of the filter member is joined to the inflatable portion.

6. The hemostatic device according to claim 1, wherein the filter member is disposed on a side of the outer surface of the band.

7. The hemostatic device according to claim 1, wherein a material of the filter member has a larger gas permeation amount per unit area than a gas permeation amount per unit area of a material of the inflatable portion.

8. The hemostatic device according to claim 1, wherein the one or more hole portions form a honeycomb structure, the honeycomb structure having a plurality of hole portions, each of the plurality of hole portions having a shape of a hexagon.

9. The hemostatic device according to claim 1, wherein the inflatable portion includes a first pressing portion configured to press the site and a second pressing portion disposed between the first pressing portion and the support plate to adjust a direction of a pressing force applied by a pressing force of the first pressing portion to a direction toward the puncture site.

10. The hemostatic device according to claim 1, wherein the band includes a support plate on which the inflatable portion is disposed, the support plate include the one or more holes, each of the one or more holes having a tapered shape from an inner surface side to an outer surface side of the support plate.

11. The hemostatic device according to claim 1, further comprising:
    an injection part configured to inject the gas into the inflatable portion, the injection part being integrally provided on the hemostatic device and includes a housing configured to house a source of gas.

12. The hemostatic device according to claim 1, wherein the band includes a support plate on which the inflatable portion is disposed, the support plate includes the one or more holes, each of the one or more holes having a tapered shape from an inner surface side to an outer surface side of the support plate.

13. The hemostatic device according to claim 12, wherein a material of the filter member has a larger gas permeation amount per unit area than a gas permeation amount per unit area of a material of the inflatable portion.

14. The hemostatic device according to claim 12, wherein the filter member and the inflatable portion are formed of a same material, the filter member including a porous layer and a skin layer having a smaller gas permeation amount per unit area than a gas permeation amount per unit area of the porous layer.

15. The hemostatic device according to claim 12 wherein the hole portion of the support plate has a honeycomb structure, the honeycomb structure having a plurality of hole portions, each of the plurality of hole portions having a shape of a hexagon.

16. The hemostatic device according to claim 12, wherein the inflatable portion includes a first pressing portion configured to press the site and a second pressing portion disposed between the first pressing portion and the support plate to adjust a direction of a pressing force applied by a pressing force of the first pressing portion to a direction toward the puncture site.

17. The hemostatic device according to claim 12, wherein the hole portion of the support plate includes one or more holes, each of the one or more holes having a tapered shape from an inner surface side to an outer surface side of the support plate.

18. A method for performing hemostasis on a puncture site of a blood vessel of a patient's limb, the method comprising:
    wrapping the band of the hemostatic device according to claim 12 around the patient's limb having the puncture site; and
    securing the band to the patient's limb in a wrapped state.

19. The method according to claim 18, further comprising:
    inflating the inflatable portion with the gas to cause the inflation portion to apply a pressing force to the puncture site.

20. A hemostatic device comprising:
    a band configured to be wrapped around a puncture site where bleeding is to be stopped, the band having one or more hole portions penetrating between an inner surface and an outer surface of the band;
    a fastener configured to secure the band to a limb in a wrapped state;
    an inflatable portion configured to be connected to the band and inflated with a gas, the inflatable portion being disposed to cover the one or more hole portions on the inner surface of the band; and
    a filter member disposed on the band to block the one or more hole portions and configured to control discharge of the gas from the inflatable portion through the one or more hole portions, and wherein the one or more hole portions form a honeycomb structure, the honeycomb structure having a plurality of hole portions, each of the plurality of hole portions having a shape of a hexagon.

* * * * *